US006470236B2

(12) United States Patent
Ohtsuki

(10) Patent No.: US 6,470,236 B2
(45) Date of Patent: Oct. 22, 2002

(54) SYSTEM AND METHOD FOR CONTROLLING MASTER AND SLAVE MANIPULATOR

(75) Inventor: Tomoyuki Ohtsuki, Kanagawa (JP)

(73) Assignee: Sony Corporation, Tokyo (JP)

(*) Notice: Subject to any disclaimer, the term of this patent is extended or adjusted under 35 U.S.C. 154(b) by 0 days.

(21) Appl. No.: 10/023,631

(22) Filed: Dec. 18, 2001

(65) Prior Publication Data

US 2002/0123825 A1 Sep. 5, 2002

(30) Foreign Application Priority Data

Dec. 19, 2000 (JP) .......................... 2000-384732

(51) Int. Cl.[7] .............................. G05B 19/04
(52) U.S. Cl. ................. 700/247; 700/245; 700/251; 700/257; 700/259; 700/258; 700/264; 600/101; 600/102; 600/117; 600/118; 600/429; 600/595; 600/126; 606/1; 606/116; 606/19; 606/130; 606/139; 606/46; 606/205; 414/1; 414/2; 701/23; 345/157; 901/8
(58) Field of Search ................. 700/245, 247, 700/251, 259, 257, 264, 258; 318/568.11; 600/102, 101, 117, 126, 109, 118, 429, 595, 407, 427, 474, 476; 606/1, 16, 130, 139, 19, 46, 167, 564, 205; 345/157; 414/2, 1; 701/23; 128/898; 901/8

(56) References Cited

U.S. PATENT DOCUMENTS

| | | | | | |
|---|---|---|---|---|---|
| 5,339,799 A | * | 8/1994 | Kami et al. | .................. | 600/117 |
| 5,841,950 A | * | 11/1998 | Wang et al. | ................. | 700/264 |
| 5,855,553 A | * | 1/1999 | Tajima et al. | ................ | 600/407 |
| 5,876,325 A | * | 3/1999 | Mizuno et al. | .............. | 600/102 |
| 5,878,193 A | * | 3/1999 | Wang et al. | ................. | 700/251 |
| 5,907,664 A | * | 5/1999 | Wang et al. | ................. | 700/251 |
| 5,911,036 A | * | 6/1999 | Wright et al. | ................ | 700/259 |
| 5,971,976 A | * | 10/1999 | Wang et al. | .................... | 606/1 |
| 6,001,108 A | * | 12/1999 | Wang et al. | ................. | 606/130 |
| 6,007,550 A | * | 12/1999 | Wang et al. | ................. | 606/139 |
| 6,063,095 A | * | 5/2000 | Wang et al. | ................. | 606/139 |
| 6,102,850 A | * | 8/2000 | Wang et al. | ................. | 600/102 |
| 6,331,181 B1 | * | 12/2001 | Tierney et al. | ............. | 606/130 |

OTHER PUBLICATIONS

Lai et al., Evaluationg control modes for constrained robotic surgery, 2000, Internet/IEEE, pp. 603–609.*
Townsend et al., Tutorial: Teleoperator slave–WAM design methodology, 1999. Internet, pp. 167–177.*
Rosen et al., Force controlled and teleoperated endoscopic grasper for minimally invaseve surgery–experemental performance evaluation, 1999, Internet, pp. 1–21.*
Bar–Cohen et al., Virtual reality robotic telesurgery simulations using MEMICA haptic system, 2001, Internet, pp. 1–8.*
Hirzinger et al., Telerobotics, 1997, internet, pp. 1–25.*
Bardorfer et al., Connecting haptic interface with a robot, 2000, Internet, pp. 1–4.*
Birglen et al., Haptic devices based on parallel mechanisms, 2001, internet, pp. 1–6.*
Goodall, 8th Annual medicine meets virtual reality: Internal conference; Envisioning healing; Interactive technology and patient–practitioner dialogue, 2000, Interner, pp. 1–7.*

(List continued on next page.)

Primary Examiner—William A. Cuchlinski, Jr.
Assistant Examiner—McDieunel Marc
(74) Attorney, Agent, or Firm—Frommer Lawrence & Haug LLP; William S. Frommer

(57) ABSTRACT

In a system and a method for remotely controlling a slave manipulator easily and highly accurately, operations of three master manipulators are consolidated, and one slave manipulator is remotely controlled in accordance with the consolidation result, thereby ensuring that the slave manipulator is moved along a target path.

31 Claims, 26 Drawing Sheets

OTHER PUBLICATIONS

DLR, Institute of robotics and mechantronics, nodate, Internet, pp. 1–2.*

DLR, Institute of robotics and mechantronics, nodate, Internet, p. 1.*

Hirzinger et al., DLR, Institute of robotics and mechantronics, nodate, Internet, pp. 1–2.*

Wei et al., DLR, Institute of robotics and mechantronics, A real-time visual servoing system for laparoscopic surgery, nodate, Internet, pp. 1–2.*

Schwertassek et al., DLR, Institute of robotics and mechantronics, nodate, Internet, pp. 1–2.*

Stone, Haptic feedback: A potted history, from telepresence to virtual reality, no date, Internet, pp. 1–7.*

Salcudean et al., A robot system for medical ultrasound, nodate, Internet, pp. 1–8.*

Cuschieri, Virtual tissue properties, no date, Internet, pp. 44–54.*

* cited by examiner (OPERATOR A)

FIG. 4
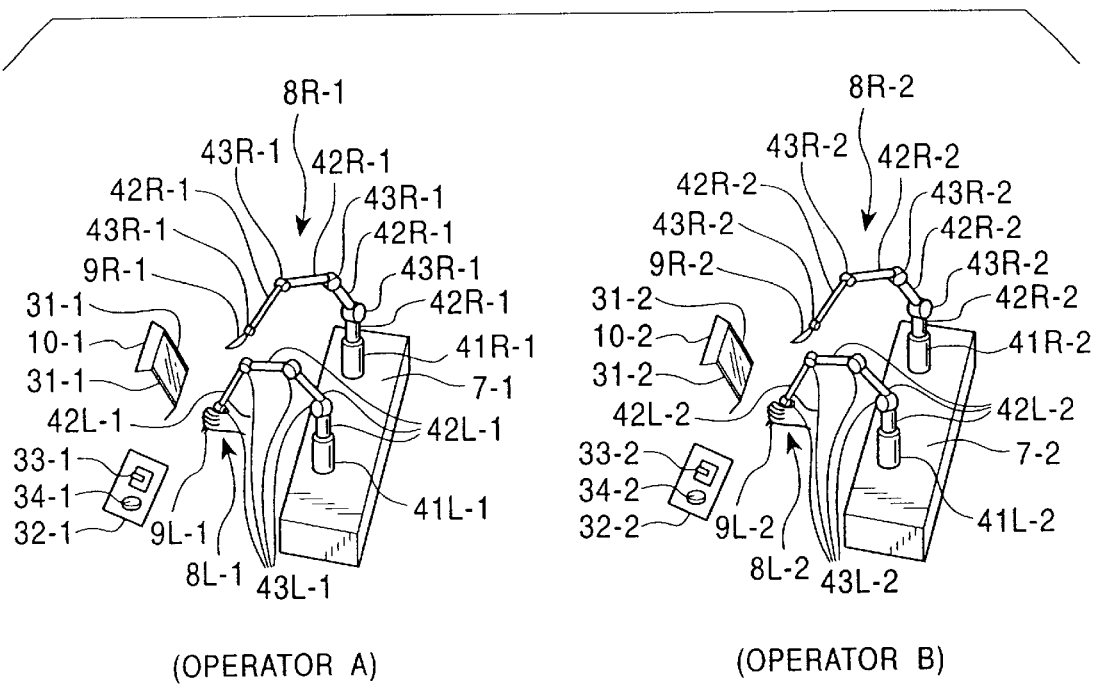
(OPERATOR A)   (OPERATOR B)
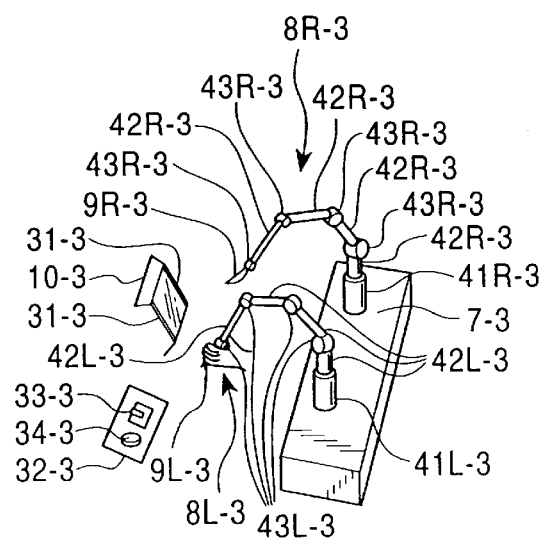
(OPERATOR C)

TARGET
TRAJECTORY

OPERATION
TRAJECTORY

OPERATOR A  OPERATOR B  OPERATOR C

MEAN
TRAJECTORY

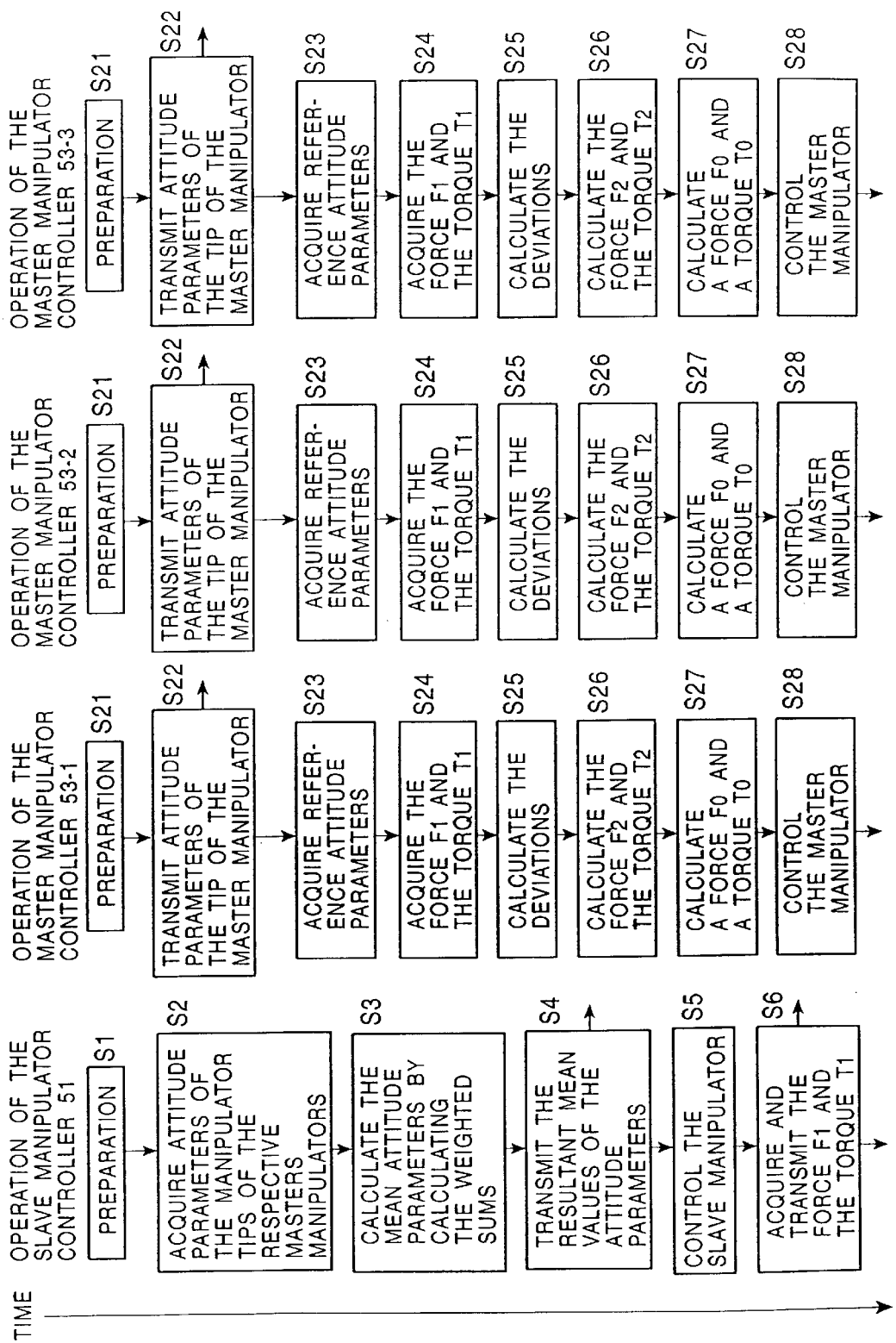

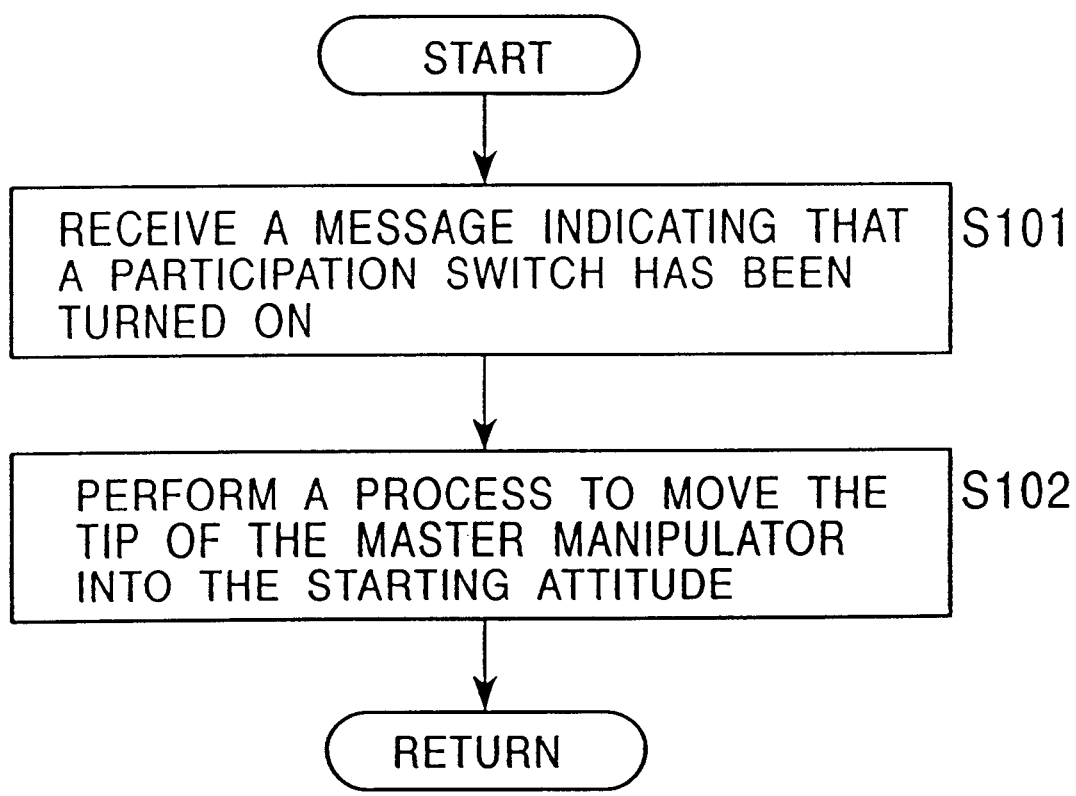

SYSTEM AND METHOD FOR CONTROLLING MASTER AND SLAVE MANIPULATOR

BACKGROUND OF THE INVENTION

1. Field of the Invention

The present invention relates to a manipulator system, a method for controlling a manipulator, a master manipulator, a method for controlling a master manipulator, a slave manipulator, a method for controlling a slave manipulator, and a storage medium. More particularly, the present invention relates to a manipulator system, a method for controlling a manipulator, a master manipulator, a method for controlling a master manipulator, a slave manipulator, a method for controlling a slave manipulator, and a storage medium, which allow the slave manipulator to be remotely controlled in an easy and accurate fashion.

2. Description of the Related Art

FIG. 1 illustrates the outer appearance of a conventional medical operation manipulator system.

A slave manipulator 3L and a slave manipulator 3R are disposed on an operating table 1. The slave manipulator 3L and the slave manipulator 3R (hereinafter, they are generically denotes as slave manipulators 3 when it is not needed to distinguish them from each other) are remotely controlled by a master manipulator 8L and a master manipulator 8R, respectively, so that a percutaneous operation is performed on a patient 2 laid (on his/her back in the example shown in FIG. 1) on the operating table.

The slave manipulator 3L is disposed on the left side (when the operating table 1 is seen from above) of the operating table 1. The slave manipulator 3L has a tip part 4L disposed on an end thereof, wherein the tip part 4L includes a treating tool such as a forceps, a knife, a suturing tool, or an injection.

The slave manipulator 3R is disposed on the right side (when the operating table 1 is seen from above) of the operating table 1. The slave manipulator 3L has a tip part 4R disposed on an end thereof, wherein the tip part 4R includes a treating tool such as a forceps, a knife, a suturing tool, or an injection.

Furthermore, a camera unit 5 including a CCD camera 6 disposed on an end thereof for taking an image of the inside of the abdominal cavity of the patient 2 is disposed on the operating table 1.

A manipulator stage 7, on which the master manipulators 8L and 8R manipulated by the operator A are disposed, is placed at a location properly apart from the operating table 1.

The master manipulator 8L is disposed on the left side (when seen by the operator at the back of whom the manipulator stage is disposed) of the manipulator stage 7. On the end of the master manipulator 8L, there is disposed a handling part 9L that is held and manipulated by the left hand of the operator A.

The master manipulator 8R is disposed on the right side of the manipulator stage 7. On the end of the master manipulator 8R, there is disposed a handling part 9R that is held and manipulated by the right hand of the operator A.

A monitor 10 is disposed near the manipulator stage 7 so that the operator A can see an image displayed on the monitor 10 when the operator A manipulates the master manipulators 8 (handling part 9). An image taken by the CCD camera 6 of the camera unit 5 is displayed on the monitor 10.

The operator A stands between the manipulator stage 7 and the monitor 10 such that the manipulator stage 7 is located at the back of the operator A and performs a percutaneous operation on the patient 2 in such a manner that, while watching the tip part 4 of the slave manipulator 3 displayed on the monitor 10, the operator A three-dimensionally manipulates the handling part 9L of the master manipulator 8L by his/her left hand thereby moving the tip part 4L of the slave manipulator 3L in synchronization with the motion of the handling part 9L and three-dimensionally manipulates the handling part 9R of the master manipulator 8R by his/her right hand thereby moving the tip part 4R of the slave manipulator 3R in synchronization with the motion of the handling part 9R.

Thus, in this system, one set of slave manipulators 3 (slave manipulators 3L and 3R) is remotely controlled by one set of master manipulators 8 (master manipulators 8L and 8R) so as to perform the percutaneous operation on the patient 2.

For example, when it is desirable to move the tip part 4 of the slave manipulator 3 along a curved path from a position A to a position B as shown in FIG. 2A (hereinafter, such a desirable path will be referred to as a target path), the operator A tries to move the handling part 9 of the master manipulator 8 along a target path corresponding the target path of the tip part 4 of the salve manipulator 3.

However, in practice, depending upon the degree of the skill of the operator A who manipulates the handling part 9, the actual path of the handling part 9 can deviate, as represented by a solid line in FIG. 2B, from the target path represented by a dotted line. The deviation of the actual path of the handling part 9 from the target path causes the path of the tip part 4 of the slave manipulator 3 to deviate from its target path.

As described above, in the system in which one slave manipulator 3 is remotely controlled by one master manipulator 8, the accuracy of the remote control greatly depends on the skill of the operator A.

That is, in the conventional system, in order to achieve high accuracy in the remote control of the slave manipulator 3, the operator A has to have great skill to operate the master manipulator 8 (handling part 9). In other words, it is not easy to achieve high accuracy in the remote control of the slave manipulator 3.

SUMMARY OF THE INVENTION

In view of the above, it is an object of the present invention to provide a technique of remotely controlling a slave manipulator using a plurality of master manipulators 8 thereby achieving high accuracy and ease in the remote control of the slave manipulator.

According to an aspect of the present invention, there is provided a manipulator system including a first master manipulator, a second master manipulator, and a slave manipulator, wherein the first master manipulator includes first detection means for detecting an absolute attitude, in a space within which the first handling part is allowed to move, of a first handling part of the first master manipulator, and first transmission means for transmitting the absolute attitude of the first handling part, the second master manipulator includes second detection means for detecting an absolute attitude, in a space within which the second handling part is allowed to move, of a second handling part of the second master manipulator, and second transmission means for transmitting the absolute attitude of the second handling part, and the slave manipulator includes first acquisition means for acquiring the absolute attitude of the first handling part transmitted from the first transmission means of the first master manipulator, and the absolute attitude of the second handling part transmitted from the second transmission means of the first master manipulator, first consolidation means for consolidating the absolute attitude of the first handling part and the absolute attitude of the second handling part, and first control means for controlling the attitude of the treating part in accordance with the result of the consolidation performed by the first consolidation means.

Preferably, the absolute attitude of the first handling part is the position and the state, of the first handling part, in a space within which the first handling part is allowed to move, and the absolute attitude of the second handling part is the position and the state, of the second handling part, in a space within which the second handling part is allowed to move.

Preferably, the first consolidation means of the slave manipulator calculates the weighted sum of the absolute attitude of the first handling part and the absolute attitude of the second handling part, using predetermined weighting factors for respective terms.

Preferably, the slave manipulator further includes third detection means for detecting a first force or a first torque applied to the treating part from the object being treated, and third transmission means for transmitting the first force or the first torque, the first master manipulator further includes second acquisition means for acquiring the first force or the first torque transmitted from the third transmission means of the slave manipulator, first determination means for determining a second force or a second torque to be perceived by the first operator, in accordance with the first force or the first torque acquired by the second acquisition means, and second control means for controlling the first handling part so that the first operator perceives the second force or the second torque, and the second master manipulator further includes third acquisition means for acquiring the first force or the first torque transmitted from the third transmission means of the slave manipulator, second determination means for determining a third force or a third torque to be perceived by the second operator, in accordance with the first force or the first torque acquired by the third acquisition means, and third control means for controlling the second handling part so that the second operator perceives the third force or the third torque.

Preferably, the slave manipulator further includes third transmission means for transmitting the result of the consolidation performed by the first consolidation means, the first master manipulator further includes second acquisition means for acquiring the result of the consolidation transmitted from the third transmission means of the slave manipulator, first calculation means for calculating the difference between the absolute attitude of the first handling part and the result of the consolidation acquired by the second acquisition means, first determination means for determining a force or a torque to be perceived by the first operator, in accordance with the result of the calculation performed by the first calculation means, and second control means for controlling the first handling part so that the first operator perceives the force or the torque determined by the first determination means, and the second master manipulator further includes second acquisition means for acquiring the result of the consolidation transmitted from the third transmission means of the slave manipulator, second calculation means for calculating the difference between the absolute attitude of the second handling part and the result of the consolidation acquired by the third acquisition means, second determination means for determining a force or a torque to be perceived by the second operator, in accordance with the result of the calculation performed by the second calculation means, and third control means for controlling the second handling part so that the second operator perceives the force or the torque determined by the second determination means.

Preferably, the slave manipulator further includes third detection means for detecting a first force or a first torque applied to the treating part from the object being treated, and third transmission means for transmitting the first force or the first torque and the result of the consolidation performed by the first consolidation means, the first master manipulator further includes second acquisition means for acquiring the first force or the first torque and the result of the consolidation transmitted from the third transmission means of the slave manipulator, first calculation means for calculating the difference between the absolute attitude of the first handling part and the result of the consolidation acquired by the second acquisition means, first determination means for determining a second force or a second torque to be perceived by the first operator, in accordance with the first force or the first torque acquired by the second acquisition means and in accordance with the difference calculated by the first calculation means, and second control means for controlling the first handling part so that the first operator perceives the second force or the second torque, and the second master manipulator further includes third acquisition means for acquiring the first force or the first torque and the result of the consolidation transmitted from the third transmission means of the slave manipulator, second calculation means for calculating the difference between the absolute attitude of the second handling part and the result of the consolidation acquired by the third acquisition means, second determination means for determining a third force or a third torque to be perceived by the second operator, in accordance with the first force or the first torque acquired by the third acquisition means and in accordance with the difference calculated by the second calculation means, and third control means for controlling the second handling part so that the second operator perceives the third force or the third torque.

The first master manipulator may further include first display control means for controlling a cue so that the first operator can operate the first handling part in synchronization with the operation of the second operator on the second handling part in accordance with the cue, and the second master manipulator may further include second display control means for controlling the cue so that the second operator can operate the second handling part in synchronization with the operation of the first operator on the first handling part in accordance with the cue.

The first master manipulator may further include first output control means for controlling a sound/voice cue so that the first operator can operate the first handling part in synchronization with the operation of the second operator on the second handling part in accordance with the sound/voice cue, and the second master manipulator may further include second output control means for controlling the sound/voice cue so that the second operator can operate the second handling part in synchronization with the operation of the first operator on the first handling part in accordance with the sound/voice cue.

Preferably, the system further includes a third master manipulator including a third handling part handled by a third operator, wherein the third master manipulator further includes third detection means for detecting a relative attitude of the third handling part with respect to a predetermined reference attitude, and third transmission means for transmitting the relative attitude of the third handling part detected by the third detection means, and wherein the first acquisition means of the slave manipulator further acquires the relative attitude of the third handling part transmitted from the third transmission means of the third master manipulator, and the first consolidation means consolidates the absolute attitude of the first handling part, the absolute attitude of the second handling part, and the relative attitude of the third handling part.

The first consolidation means of the slave manipulator may calculate the weighted sum of the absolute attitude of the first handling part, the absolute attitude of the second handling part, and the relative attitude of the third handling part, using predetermined weighting factors for respective terms.

The slave manipulator may further include fourth detection means for detecting a first force or a first torque applied to the treating part from the object being treated, and fourth transmission means for transmitting the first force or the first torque, the first master manipulator may further include second acquisition means for acquiring the first force or the first torque transmitted from the fourth transmission means of the slave manipulator, third acquisition means for acquiring the absolute attitude of the second handling part transmitted of the second transmission means of the second master manipulator, second consolidation means for consolidating the absolute attitude of the first handling part and the absolute attitude of the second handling part, first calculation means for calculating the difference between the absolute attitude of the first handling part and the result of the consolidation performed by the second consolidation means, first determination means for determining a second force or a second torque to be perceived by the first operator, in accordance with the first force or the first torque acquired by the second acquisition means and in accordance with the difference calculated by the first calculation means, and second control means for controlling the first handling part so that the first operator perceives the second force or the second torque, the second master manipulator may further include second acquisition means for acquiring the first force or the first torque transmitted from the fourth transmission means of the slave manipulator, fifth acquisition means for acquiring the absolute attitude of the first handling part transmitted of the first transmission means of the first master manipulator, third consolidation means for consolidating the absolute attitude of the second handling part and the absolute attitude of the first handling part, second calculation means for calculating the difference between the absolute attitude of the second handling part and the result of the consolidation performed by the third consolidation means, second determination means for determining a third force or a third torque to be perceived by the second operator, in accordance with the first force or the first torque acquired by the fourth acquisition means and in accordance with the difference calculated by the second calculation means, and third control means for controlling the second handling part so that the second operator perceives the third force or the third torque, and the third master manipulator may include sixth acquisition means for acquiring the first force or the first torque transmitted from the fourth transmission means of the slave manipulator, third determination means for determining a fourth force or a fourth torque to be perceived by the third operator, in accordance with the first force or the first torque acquired by the sixth acquisition means and in accordance with the relative attitude of the third handling part, and fourth control means for controlling the third handling part so that the third operator perceives the fourth force or the fourth torque.

The first master manipulator may further include seventh acquisition means for acquiring the relative attitude of the third handling part transmitted from the third transmission means of the third master manipulator, the first determination means may determine the second force or the second torque such that if a value corresponding to the relative attitude of the third handling part is smaller than a predetermined threshold value, the second force or the second torque is determined in accordance with the first force or the first torque and the result of the consolidation performed by the second consolidation means, however if the value corresponding to the relative attitude of the third handling part is equal to or greater than the predetermined threshold value, the second force or the second torque is determined in accordance with only the result of the consolidation performed by the second consolidation means, the second master manipulator may further include eighth acquisition means for acquiring the relative attitude of the third handling part transmitted from the third transmission means of the third master manipulator, the second determination means may determine the third force or the third torque such that if the value corresponding to the relative attitude of the third handling part is smaller than the predetermined threshold value, the third force or the third torque is determined in accordance with the first force or the first torque and the result of the consolidation performed by the third consolidation means, however if the value corresponding to the relative attitude of the third handling part is equal to or greater than the predetermined threshold value, the third force or the third torque is determined in accordance with only the result of the consolidation performed by the third consolidation means, and the third determination means of the third master manipulator may determine the fourth force or the fourth torque such that if the value corresponding to the relative attitude of the third handling part is smaller than the predetermined threshold value, the fourth force or the fourth torque is determined in accordance with only the relative attitude of the third handling part, however if the value corresponding to the relative attitude of the third handling part is equal to or greater than the predetermined threshold value, the fourth force or the fourth torque is determined in accordance with the relative attitude of the third handling part and the first force or the first torque.

According to another aspect of the present invention, there is provided a method of controlling a manipulator, including a first detection step of detecting an absolute attitude, in a space within which the first handling part is allowed to move, of the first handling part of the first master manipulator; a first transmission step of transmitting the absolute attitude of the first handling part; a second detection step of detecting an absolute attitude, in a space within which the second handling part is allowed to move, of the second handling part of the second master manipulator; a second transmission step of transmitting the absolute attitude of the second handling part; a first acquisition step of acquiring the absolute attitude of the first handling part transmitted in the first transmission step and the absolute attitude of the second handling part transmitted in the second transmission step; a first consolidation step of consolidating the absolute attitude of the first handling part and the absolute attitude of the second handling part; and a first control step of controlling the treating part in accordance with the result of the consolidation performed in the first consolidation step.

According to still another aspect of the present invention, there is provided a first storage medium in which is stored a program including a first detection step of detecting an absolute attitude, in a space within which the first handling part is allowed to move, of the first handling part of the first master manipulator; a first transmission step of transmitting the absolute attitude of the first handling part; a second detection step of detecting an absolute attitude, in a space within which the second handling part is allowed to move, of the second handling part of the second master manipulator; a second transmission step of transmitting the absolute attitude of the second handling part; a first acquisition step of acquiring the absolute attitude of the first handling part transmitted in the first transmission step and the absolute attitude of the second handling part transmitted in the second transmission step; a first consolidation step of consolidating the absolute attitude of the first handling part and the absolute attitude of the second handling part; and a first control step of controlling the treating part in accordance with the result of the consolidation performed in the first consolidation step.

In the above-described manipulator system, manipulator control method, and first storage medium in which the program is stored, the absolute attitude, in the space within which the first handling part is allowed to move, of the first handling part of the first master manipulator is detected, the absolute attitude of the first handling part is transmitted, the absolute attitude, in the space within which the second handling part is allowed to move, of the second handling part of the second master manipulator is detected, the absolute attitude of the second handling part is transmitted, the absolute attitude of the transmitted first handling part and the absolute attitude of the transmitted second handling part are acquired, the absolute attitude of the first handling part and the absolute attitude of the second handling part are consolidated, and the attitude of the treating part is controlled in accordance with the consolidation result.

According to still another aspect of the present invention, there is provided a master manipulator comprising detection means for detecting the attitude of a handling part; and transmission means for transmitting the attitude of the handling part to a slave manipulator thereby allowing the slave manipulator to control a treating part of the slave manipulator so as to process an object in accordance with a result of consolidation of the attitude of the handling part and the attitude of a handling part of another master manipulator supplied from said another master manipulator.

According to still another aspect of the present invention, there is provided a method for controlling a master manipulator, the method comprising a detection step for detecting the attitude of a handling part; and a transmission step for transmitting the attitude of the handling part to a slave manipulator thereby allowing the slave manipulator to control a treating part of the slave manipulator so as to process an object in accordance with a result of consolidation of the attitude of the handling part and the attitude of a handling part of another master manipulator supplied from said another master manipulator.

According to still another aspect of the present invention, there is provided a second storage medium in which is stored a program comprising a detection step for detecting the attitude of a handling part; and a transmission step for transmitting the attitude of the handling part to a slave manipulator thereby allowing the slave manipulator to control a treating part of the slave manipulator so as to process an object in accordance with a result of consolidation of the attitude of the handling part and the attitude of a handling part of another master manipulator supplied from said another master manipulator.

In the above-described master manipulator, the method for controlling the master manipulator, and the second storage medium in which the program is stored, the attitude of the handling part is detected, the detected attitude of the handling part is transmitted to the slave manipulator, and the slave manipulator is controlled in accordance with the consolidation of the attitude of the handling part and the attitude of the handling part of another master manipulator supplied from said another master manipulator so that the treating part of the slave manipulator correctly processes the object.

According to still another aspect of the present invention, there is provided a slave manipulator comprising acquisition means for acquiring the attitude of a first handling part of a first master manipulator transmitted from the first master manipulator and the attitude of a second handling part of a second master manipulator transmitted from the second master manipulator; consolidation means for consolidating the attitude of the first handling part and the attitude of the second handling part; and control means for controlling the attitude of the treating part in accordance with the result of the consolidation performed by the consolidation means.

According to still another aspect of the present invention, there is provided a method for controlling a slave manipulator, comprising an acquisition step for acquiring the attitude of a first handling part of a first master manipulator transmitted from the first master manipulator and the attitude of a second handling part of a second master manipulator transmitted from the second master manipulator; a consolidation step for consolidating the attitude of the first handling part and the attitude of the second handling part; and a control step for controlling the attitude of the treating part in accordance with the result of the consolidation performed in the consolidation step.

According to still another aspect of the present invention, there is provided a third storage medium in which is stored a program comprising an acquisition step for acquiring the attitude of a first handling part of a first master manipulator transmitted from the first master manipulator and the attitude of a second handling part of a second master manipulator transmitted from the second master manipulator; a consolidation step for consolidating the attitude of the first handling part and the attitude of the second handling part; and a control step for controlling the attitude of the treating part in accordance with the result of the consolidation performed in the consolidation step.

In the above-described slave manipulator, method for controlling the slave manipulator, and third storage medium in which the program is stored, the attitude of the first handling part of the first master manipulator transmitted from the first master manipulator and the attitude of the second handling part of the second master manipulator transmitted from the second master manipulator are acquired, the attitudes of the first and second handling parts are consolidated, and the attitude of the treating part is controlled in accordance with the consolidation result.

BRIEF DESCRIPTION OF THE DRAWINGS

FIG. 4 is a diagram illustrating the outward appearance of master manipulators in the medical operation manipulator system according to the present invention;

FIG. 18 is a diagram illustration the relationship among the operations of slave manipulator control unit 51 and the master manipulator control units 53;

FIG. 25 is a flow chart illustrating the details of step S91 shown in FIG. 24;

DESCRIPTION OF THE PREFERRED EMBODIMENTS

Figure 1:
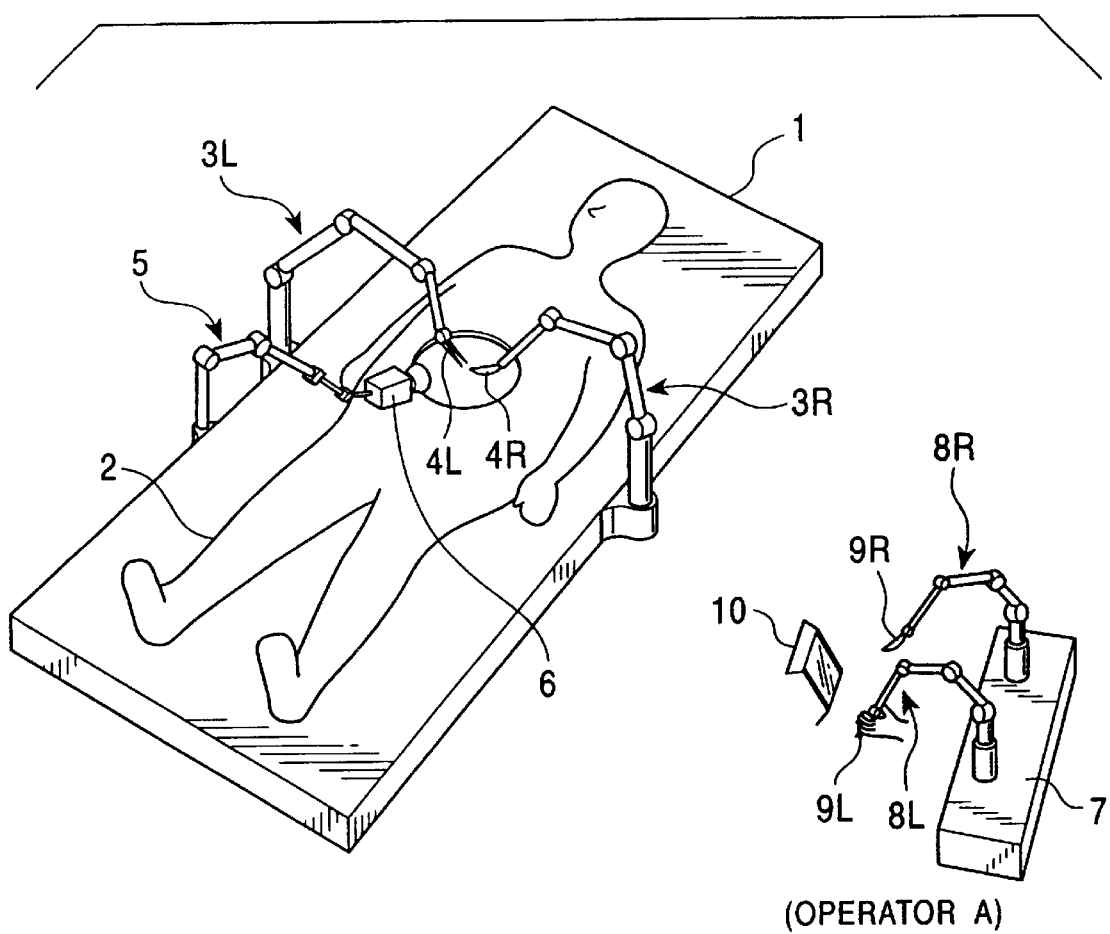
FIG. 1 is a diagram illustrating the outward appearance of a conventional manipulator system for a medical operation.
Figure 3:
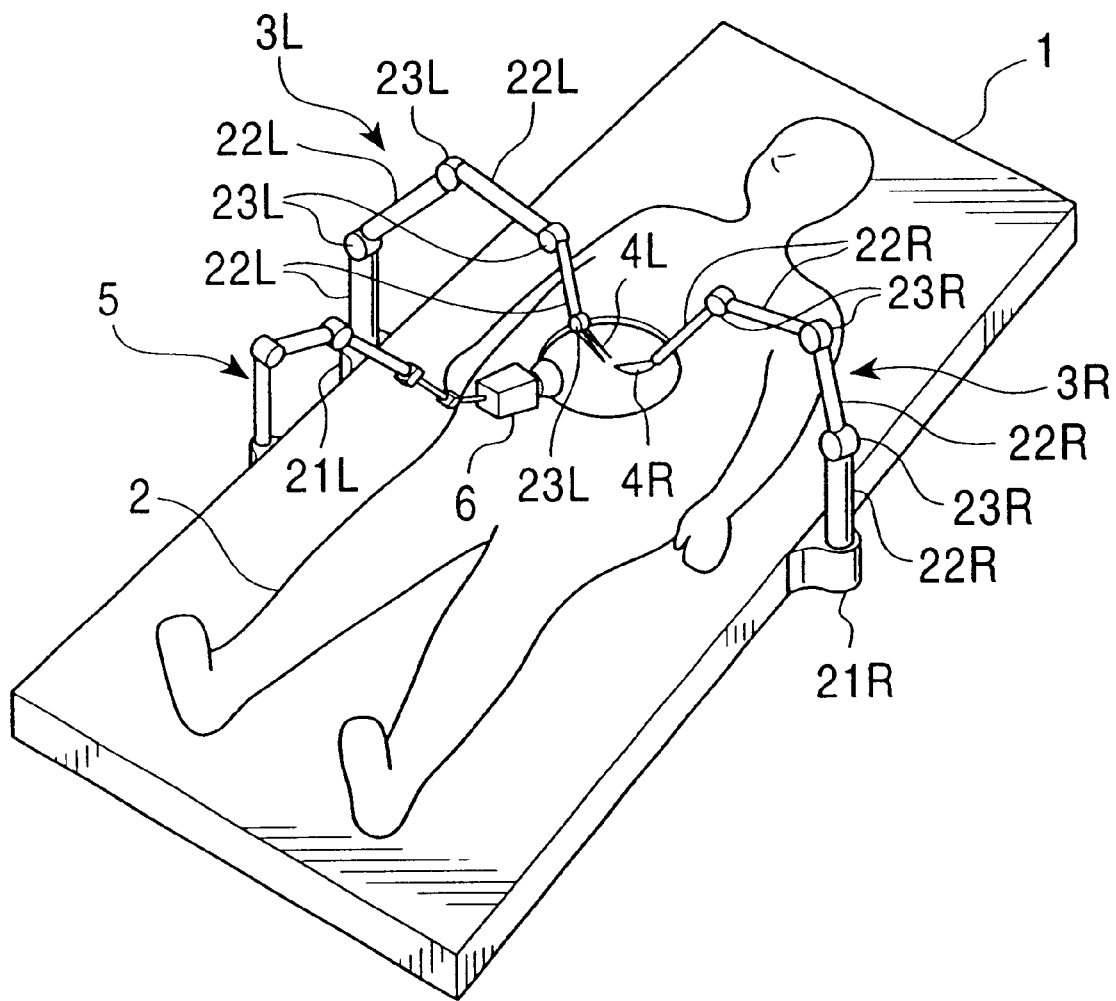
FIG. 3 is a diagram illustrating the outward appearance of a slave manipulator in a medical operation manipulator system according to an embodiment of the present invention.

FIG. 3 illustrates the outward appearance of a medical operation manipulator system according to an embodiment of the present invention, and FIG. 4 illustrates the outward appearance of master manipulators in the system. In FIG. 3, similar parts to those in FIG. 1 are denoted by similar reference numerals. In FIG. 4, similar parts are denoted by similar reference numerals with a suffix such as "–1", A slave manipulator 3L is disposed on a base 21L fixed to an operating table 1 and includes a plurality of arms 22L and driving units 23L, which are combined into an articulated structure.

On an end of the slave manipulator 3L, there is disposed a tip part 4L including a treating tool such as a forceps, a knife, a suturing tool, or an injection. The tip part 4L also includes a sensor (not shown) for detecting a force F1 (the magnitude and the direction of the force F1) or a torque T1 (the magnitude and the direction of the torque T1) applied to the end of the tip part 4L from the outside.

A slave manipulator 3R is disposed on a base 21R fixed to the operating table 1 and includes a plurality of arms 22R and driving units 23R, which are combined into an articulated structure.

On an end of the slave manipulator 3R, there is disposed a tip part 4R including a treating tool such as a forceps, a knife, a suturing tool, or an injection. The tip part 4R also includes a sensor (not shown) for detecting a force F1 or a torque T1 applied to the end of the tip part 4R from the outside.

The camera unit 5 is disposed on a base 31 fixed to the operating table, at a position slightly shifted from the position of the base 21L of the slave manipulator in a direction toward the foots of a patient, and the camera unit 5 includes a plurality of arms 32 and driving units 33 combined into an articulated structure. In FIG. 3, for the purpose of simplicity, reference numerals for the base 31, the arms 32, and the driving units 33 are not shown.

In FIG. 4, the manipulator stages 7-1 to 7-3 are disposed at locations properly spaced from the operating table 1. The master manipulators 8L-1 and 8R-1 are disposed on the manipulator stage 7-1, the master manipulators 8L-2 and 8R-2 are disposed on the manipulator stage 7-2, and the master manipulators 8L-3 and 8R-3 are disposed on the manipulator stage 7-3.

In the following description, when it is not needed to distinguish the master manipulators 8L-1 and 8R-1 from each other, they are generically denoted as a master manipulator 8-1. That is, the whole of the master manipulators disposed on the manipulator stage 7-1 are denoted as the master manipulator 8-1. For the other manipulators, similar notations are used.

When it is not needed to distinguish the master manipulator 8L-1, the master manipulator 8L-2, and the master manipulator 8L-3 from each other, they are generically denoted as a master manipulator 8L. That is, master manipulators disposed on the left side (when seen by an operator at the back of whom a master manipulator is disposed) of the respective manipulator stages 7-1 to 7-3 are generically denoted as a master manipulator 8L.

When it is not needed to distinguish the master manipulator 8R-1, the master manipulator 8R-2, and the master manipulator 8R-3 from each other, they are generically denoted as a master manipulator 8R. That is, master manipulators disposed on the right side (when seen by an operator at the back of whom a master manipulator is disposed) of the respective manipulator stages 7-1 to 7-3 are generically denoted as a master manipulator 8R.

When it is not needed to distinguish a master manipulator 8L and a master manipulator 8R they are generically denoted as a master manipulator 8. That is, any one of the master manipulator is denoted simply as a master manipulator 8, when it is not needed to distinguish an individual master manipulator from the other.

The master manipulators are described in further detail below.

A master manipulator 8L-1 is disposed on a base 41L-1 fixed to the manipulator stage 7-1 and includes a plurality of arms 42L-1 and driving units 43L-1, which are combined into an articulated structure. A master manipulator 8R-1 is disposed on a base 41R-1 fixed to the manipulator stage 7-1 and includes a plurality of arms 42R-1 and driving units 43R-1, which are combined into an articulated structure.

As in the system shown in FIG. 1, the master manipulator 8-1 is operated by an operator A. More specifically, the handling part 9L-1 of the master manipulator 8L-1 is handled three-dimensionally by the left hand of the operator A, and the handling part 9R-1 of the master manipulator 8R-1 is handled three-dimensionally by the right hand of the operator A.

A monitor 10-1 is disposed near the manipulator stage 7-1 so that the operator A can see an image displayed on the monitor 10-1 when the operator A manipulates the master manipulators 8-1. The monitor 10-1 is adapted to display an image taken by the CCD camera 6 of the camera unit 5 and a synchronization screen that will be described later. A speaker 31-1 is disposed on the monitor 10-1 to output, for example, a synchronization sound/voice that will be described later.

A switch unit 32-1 is disposed near the manipulator stage 7-1 so that the operator A can operate the switch unit 32-1 while manipulating the master manipulators 8-1. The switch unit 32-1 includes a participation switch 33-1 and a synchronization start switch 34-1, which will be described in detail later.

A master manipulator 8L-2 is disposed on a base 41L-2 fixed to the manipulator stage 7-2 and includes a plurality of arms 42L-2 and driving units 43L-2, which are combined into an articulated structure. A master manipulator 8R-2 is disposed on a base 41R-2 fixed to the manipulator stage 7-2 and includes a plurality of arms 42R-2 and driving units 43R-2, which are combined into an articulated structure.

The master manipulators 8-2 are operated by the operator B. More specifically, the handling part 9L-2 of the master manipulator 8L-2 is handled three-dimensionally by the left hand of the operator B, and the handling part 9R-2 of the master manipulator 8R-2 is handled three-dimensionally by the right hand of the operator B.

A monitor 10-2 is disposed near the manipulator stage 7-2 so that the operator B can see an image displayed on the monitor 10-2 when the operator B manipulates the master manipulators 8-2. The monitor 10-2 is adapted to display an image taken by the CCD camera 6 of the camera unit 5 and a synchronization screen that will be described later. A speaker 31-2 is disposed on the monitor 10-2 to output, for example, a synchronization sound/voice.

A switch unit 32-2 is disposed near the manipulator stage 7-2 so that the operator B can operate the switch unit 32-2 while manipulating the master manipulators 8-2. The switch unit 32-2 includes a participation switch 33-2 and a synchronization start switch 34-2.

A master manipulator 8L-3 is disposed on a base 41L-3 fixed to the manipulator stage 7-3 and includes a plurality of arms 42L-3 and driving units 43L-3, which are combined into an articulated structure. A master manipulator 8R-3 is disposed on a base 41R-3 fixed to the manipulator stage 7-3 and includes a plurality of arms 42R-3 and driving units 43R-3, which are combined into an articulated structure.

The master manipulators 8-3 are operated by the operator C. More specifically, the handling part 9L-3 of the master manipulator 8L-3 is handled three-dimensionally by the left hand of the operator C, and the handling part 9R-3 of the master manipulator 8R-3 is handled three-dimensionally by the right hand of the operator C.

A monitor 10-3 is disposed near the manipulator stage 7-3 so that the operator C can see an image displayed on the monitor 10-3 when the operator C manipulates the master manipulators 8-3. The monitor 10-3 is adapted to display an image taken by the CCD camera 6 of the camera unit 5 and a synchronization screen that will be described later. A speaker 31-3 is disposed on the monitor 10-3 to output, for example, a synchronization sound/voice.

A switch unit 32-3 is disposed near the manipulator stage 7-3 so that the operator C can operate the switch unit 32-3 while manipulating the master manipulators 8-3. The switch unit 32-3 includes a participation switch 33-3 and a synchronization start switch 34-3.

When the operator tries to operate the handling part 9 of the master manipulator 8 so as to move the operating point of the handling part 9 through a desired point indicated by coordinates (x, y, z) while maintaining the handling part 9 in a desired state (for example, with desired angles in terms of rolling, pitching, and yawing), there is a possibility that the actual path deviates from the target path.

Figure 5:
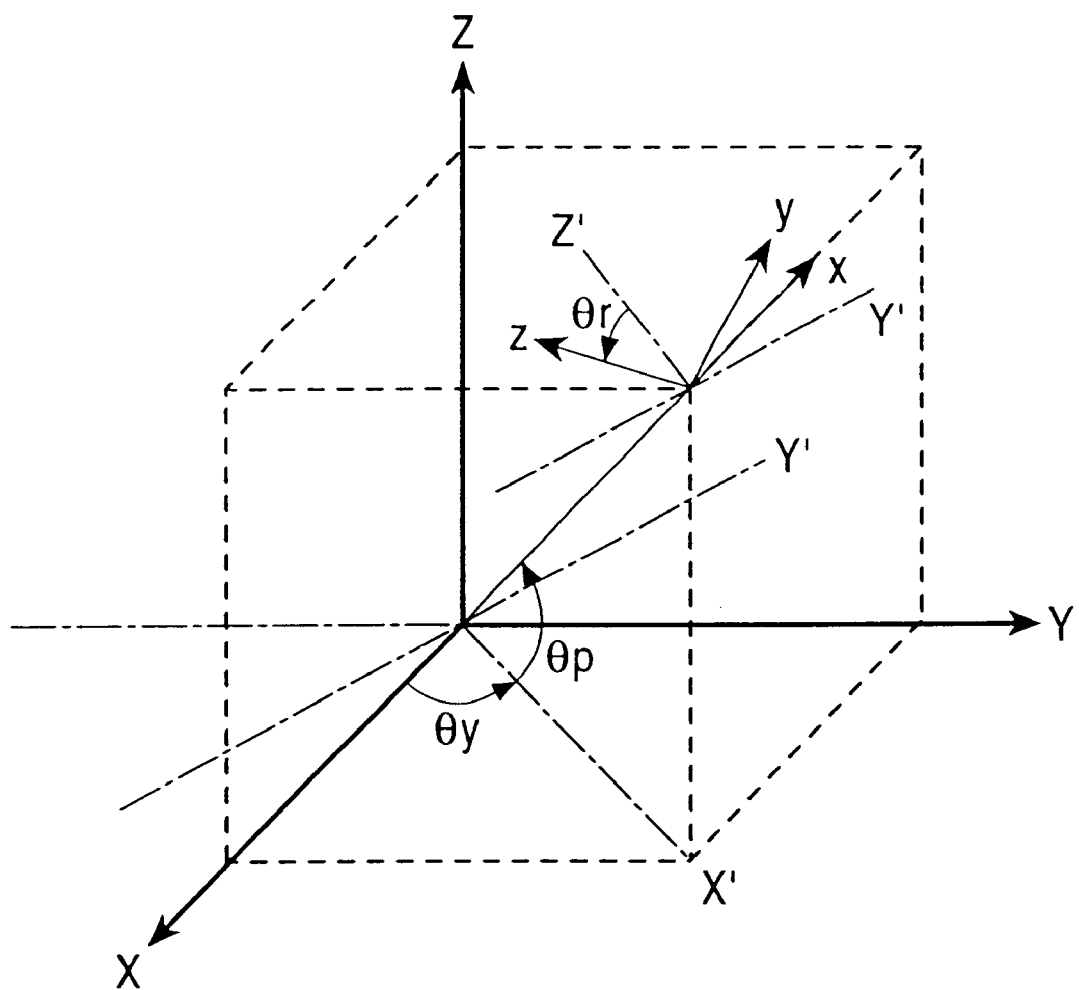
FIG. 5 is a diagram illustrating yawing, pitching, and rolling.

Herein, the yawing refers to a rotation of the X axis and Y axis about the X axis as shown in FIG. 5 in which the rotation angle due to the yawing is denoted by $\theta y$. The pitching refers to a rotation of the Z axis and the X axis rotated by $\theta y$ due to the yawing (the rotated X axis is denoted as X' axis in FIG. 5) about the Y axis rotated due to the yawing (the rotated Y axis is denoted as Y' axis in FIG. 5). The rotation angle due to the pitching is denoted by $\theta p$ in FIG. 5. The rolling refers to a rotation of the Y axis rotated by $\theta y$ due to the yawing (the rotated Y axis is denoted as Y' axis in FIG. 5) and the Z axis rotated by $\theta p$ due to the pitching (the rotated Z axis is denoted as Z' axis in FIG. 5) about the X axis rotated by $\theta y$ due to the yawing and further by $\theta p$ due to the pitching (the rotated X axis is denoted by x axis in FIG. 5). The rotation angle due to the rolling is denoted by $\theta r$ in FIG. 5.

Figure 6A:
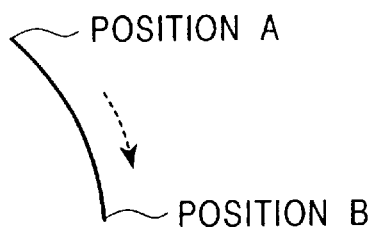
FIGS. 6A, 6B, and 6C are diagrams illustrating the attitude of the tip part of the slave manipulator and the attitudes of the handling parts of the master manipulators.

For example, when it is desirable to move the tip part 4 of the slave manipulator 3 along a curved path (target path) from a position A to a position B as shown in FIG. 6A, the operators A to C try to move the handling parts 9-1 to 9-3 of the master manipulators 8-1 to 8-3 along their own target paths corresponding to the target path of the tip part 4 of the salve manipulator 3. (The target paths of the master manipulators 8 may differ from each other depending upon the sizes and the structures of the slave manipulator 3 and the master manipulators. However, in this specific example, for the purpose of simplicity, the target paths of the master manipulators 8 are assumed to be equal to each other.) However, in practice, depending upon the degrees of the skill of the operators A to C who manipulates the master manipulators 8 (handling parts 9), the actual paths of the handling parts 9 can deviate, as represented by solid lines in FIG. 6B, from the target paths represented by dotted lines.

Usually, the deviations from the target paths occur randomly (not systematically). Therefore, if the actual paths of the respective handling parts 9 (operated by the operators A, B, and C) are averaged (FIG. 6B), the result becomes closer to the target path.

Figure 6B:
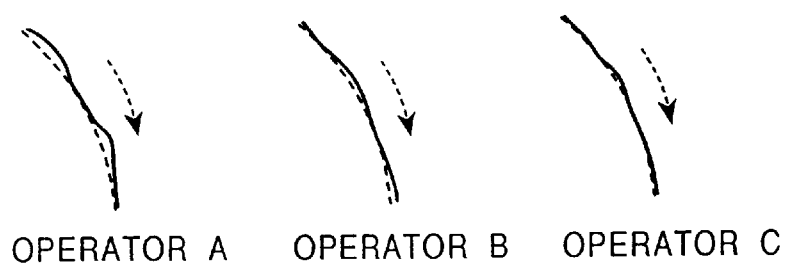
Figure 6C:

In the present invention, in view of the above, as shown in FIG. 4, the operations of the plurality (three in this example) of master manipulators 8-1 to 8-3 (master manipulators 8L-1 to 8L-3 or master manipulators 8R-1 to 8R-3) are consolidated (by means of averaging, for example), and one slave manipulator 3 (the slave manipulator 3L or the slave manipulator 3R) is remotely controlled in accordance with the result of the consolidation thereby allowing the tip part 4 of the slave manipulator 3 to move along a path closer to its target path (FIG. 6C).

In FIG. 6A, a dotted arrow indicates a direction in which the tip part 4 of the slave manipulator 3 should be moved along the target path. In FIG. 6B, dotted arrows indicate directions in which the handling parts 9 are moved. In FIG. 6C, a dotted arrow indicates a direction in which the tip part 4 is moved.

Figure 7:
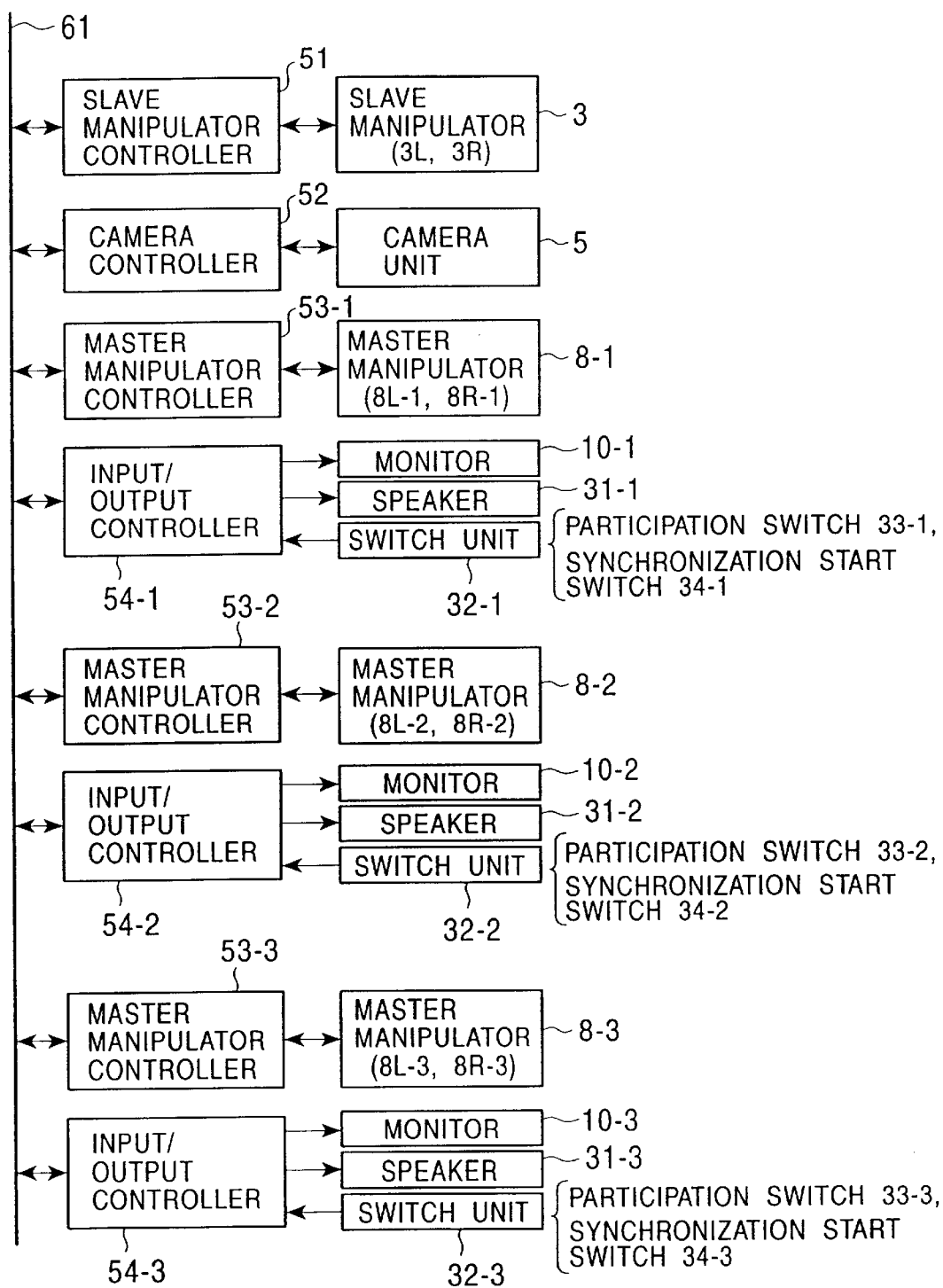
FIG. 7 is a block diagram illustrating an example of the internal configuration of the medical operation manipulator system according to the present invention.

FIG. 7 illustrates an internal configuration of an operation manipulator system.

A slave manipulator control unit 51 for controlling the slave manipulator 3 and a camera controller 52 for controlling the camera unit 5 are connected to a network 61.

Furthermore, A master manipulator control unit 53-1 for controlling the master manipulator 8-1, a master manipulator control unit 53-2 for controlling the master manipulator 8-2, and a master manipulator control unit 53-3 for controlling the master manipulator 8-3 are also connected to the network 61.

An input/output controller 54-1 for controlling the monitor 10-1, the speaker 31-1, and the switch unit 32-1, an input/output controller 54-2 for controlling the monitor 10-2, the speaker 31-2, and the switch unit 32-2, and an input/output controller 54-3 for controlling the monitor 10-3, the speaker 31-3, and the switch unit 32-3 are also connected to the network 61.

The slave manipulator control unit 51 acquires the attitude parameters of the handling parts 9-1 to 9-3 of the master manipulators 8-1 to 8-3 transmitted from the master manipulator control units 53-1 to 53-3 over the network 61 and determines the attitude parameters of the tip part 4 of the salve manipulator 3 in accordance with the acquired attitude parameters.

The attitude parameters of the tip part 4 of the slave manipulator 3 include three values of coordinates indicating the position of the tip part 4 (operating point), that is, a X coordinate, a Y coordinate, and a Z coordinate, and further include three values θy, θp, and θr indicating the state of the tip part 4. That is, the attitude parameters of the tip part 4 include a total of six parameters. The position of the tip part 4 is represented with respect to a reference position (for example, the center of a facing surface between the base 21 and the operating table 1) in a space within which the tip part 4 is allowed to move. The state of the tip part 4 is represented with respect to a reference state in which, for example, X, Y, and Z axes of an orthogonal coordinate system fixed to the tip part 4 become coincident with x, Y, and X axes of an orthogonal coordinate system fixed to the space in which the tip part 4 moves.

The attitude parameters of the handling part 9 of the master manipulator 8 include three values of coordinates indicating the position of the handling part 9 (operating point), that is, a X coordinate, a Y coordinate, and a X coordinate, and further include three values θy, θp, and θr indicating the state of the handling part 9. That is, the attitude parameters of the handling part 9 include a total of six parameters. The position of the handling part 9 is represented with respect to a reference position (for example, the center of a facing surface between the base 41 and the manipulator stage 7) in a space within which the handling part 9 is allowed to move. The state of the handling part 9 is represented with respect to a reference state in which, for example, X, Y, and Z axes of an orthogonal coordinate system fixed to the handling part 9 become coincident with X, Y, and X axes of an orthogonal coordinate system fixed to the space in which the handling part 9 moves.

The slave manipulator control unit 51 controls the slave manipulator 3 such that the tip part 4 of the slave manipulator 3 has a position and a state (hereinafter, the position and the state will be generically referred to as the attitude) corresponding to the calculated attitude parameters. The slave manipulator control unit 51 transmits the calculated attitude parameters (of the tip part) via the network 61.

The slave manipulator control unit 51 also transmits the force F1 or the torque T1 applied to the tip part 4 of the slave manipulator 3 via the network 61.

Figure 8:
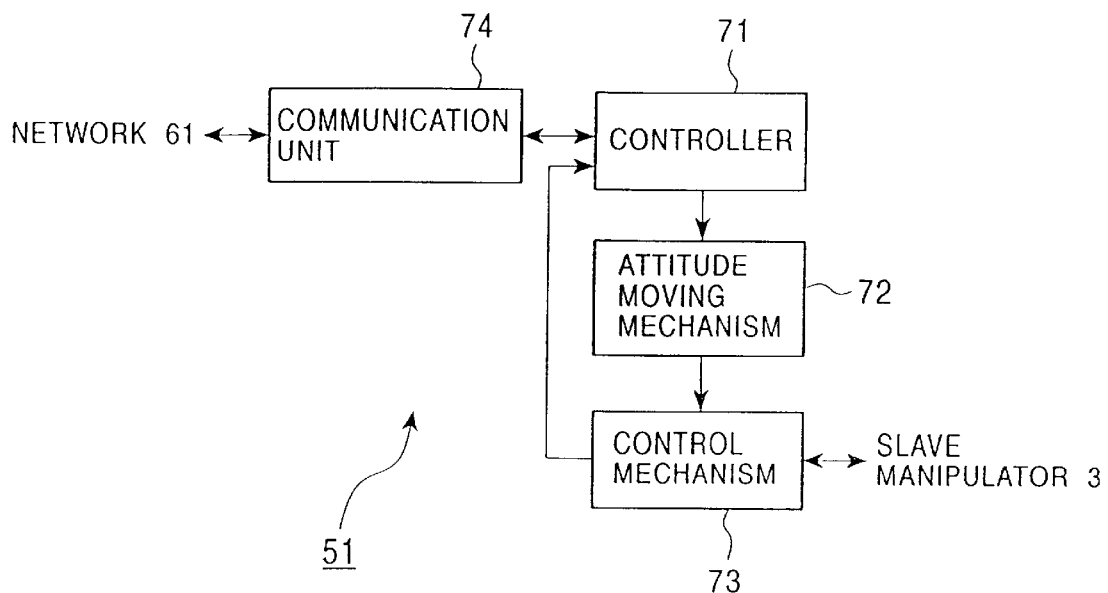
FIG. 8 is a block diagram illustrating an example of the configuration of a slave manipulator control unit 51 shown in FIG. 7.

FIG. 8 illustrates an example of the structure of the slave manipulator control unit 51.

A controller 71 calculates attitude parameters of the tip part 4 of the slave manipulator 3 in accordance with the attitude parameters of the master manipulators 8-1 to 8-3 received by a communication unit 74 via the network 61 from the respective master manipulator controllers 53-1 to 53-3. The controller 71 supplies the calculated attitude parameters to an attitude changing mechanism 72 and transmits them over the network 61 from the communication unit 74.

The controller 71 receives, from a control mechanism 73, data indicating a force F1 or a torque T1 applied from the outside to the tip part 4 of the slave manipulator 3 and transmits the received data over the network 61 via the communication unit 74.

The attitude changing mechanism 72 produces attitude change information used to move the tip part 4 of the slave manipulator 3 from its current attitude to an attitude specified by the attitude parameters supplied from the controller 71, and transmits the produced attitude change information to the control mechanism 73.

In accordance with the attitude change information received from the attitude changing mechanism 72, the control mechanism 73 produces a control signal and supplies it to the driving unit 23 of the slave manipulator 3. The driving unit 23 drives the arm 22 in accordance with the supplied control signal such that the tip part 4 has an attitude corresponding to the attitude parameters calculated by the controller 71.

The control mechanism 73 acquires a force F1 or a torque T1 applied from the outside to the tip part 4 of the slave manipulator 3 and supplies data indicating the force F1 or the torque T1 to the controller 71.

Referring again to FIG. 7, the camera controller 52 transmits image data outputted from the CCD camera 6 of the camera unit 5 to the input/output controllers 54-1 to 54-3 via the network 61.

The master manipulator controller 53-1 detects the attitude parameters of the handling part 9-1 of the master manipulator 8-1 and transmits the detected attitude parameters over the network 61.

The master manipulator control unit 53-1 acquires the attitude parameters of the tip part 4 of the slave manipulator 3, transmitted over the network 61 from the slave manipulator control unit 51, as reference parameters used to calculate the differences between the attitude parameters of the handling part 9-1 of the master manipulator 8-1 and the reference parameters. The master manipulator control unit 53-1 also acquires the force F1 or the torque T1 applied to the tip part 4.

The master manipulator control unit 53-1 calculates the differences between the detected attitude parameters of the handling part 9-1 of the master manipulator 8-1 and the reference attitude parameters acquired, and also calculates the force Fo or the torque To to be perceived by the operator A in accordance with the calculated differences and the acquired force F1 or the torque T1.

The master manipulator controller 53-1 controls the master manipulator 8-1 such that the operator A, who operates the handling part 9-1 of the master manipulator 8-1, perceives a force or a torque equal to the calculated force Fo or torque To.

Figure 9:
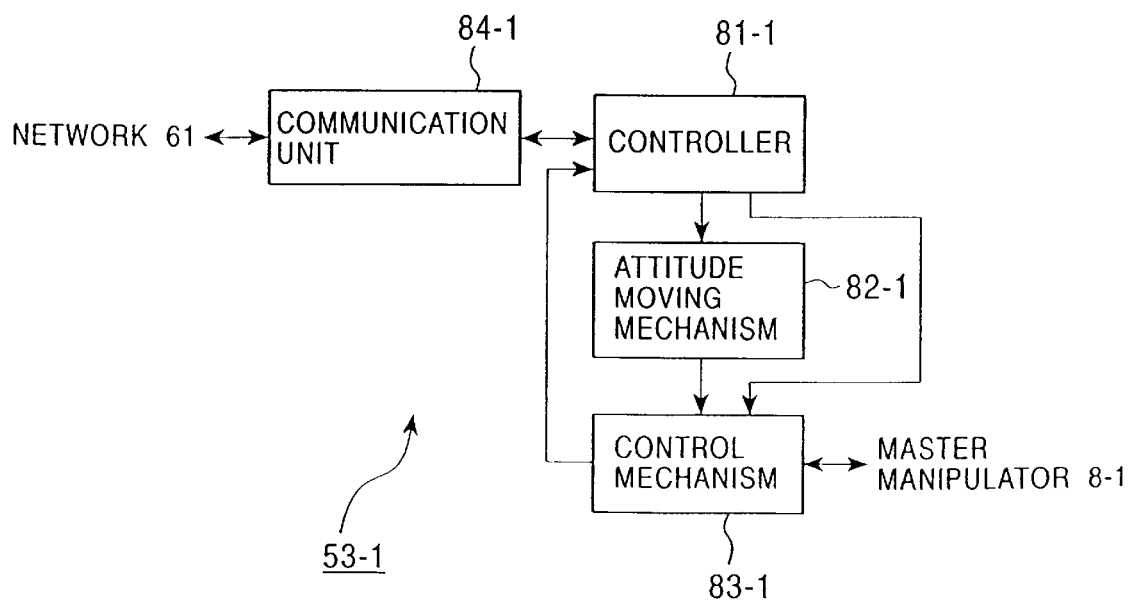
FIG. 9 is a block diagram illustrating an example of the configuration of a master manipulator control unit 53-1 shown in FIG. 7.

FIG. 9 illustrates an example of the structure of the master manipulator control unit 53-1.

The controller 81-1 receives the attitude parameters of the handling part 9-1 of the master manipulator 8-1 from the control mechanism 83-1 and transmits the received attitude parameters over the network 61 via the communication unit 84-1.

The controller 81-1 calculates the force Fo and the torque To in accordance with the attitude parameters (of the tip part 4 of the slave manipulator 3) transmitted over the network 61 from the slave manipulator control unit 51 and acquired via the communication unit 84-1 and in accordance with the force F1 and the torque T1 (applied to the tip part 4). The calculated force Fo and the torque To are supplied from the controller 81-1 to the control mechanism 83-1.

The control mechanism 83-1 produces a control signal in accordance with the force Fo and the torque To supplied from the controller 81-1 and transmits the produced control signal to the driving unit 43-1 of the master manipulator 81. The driving unit 43-1 drives the arm 42-1 in accordance with the control signal such that the handling part 9-1 of the master manipulator 8-1 provides the force Fo and the torque To calculated by the controller 81-1.

The control mechanism 83-1 detects the attitude parameters of the handling part 9-1 of the master manipulator 8-1 and supplies the detected attitude parameters to the controller 81-1.

Figure 10:
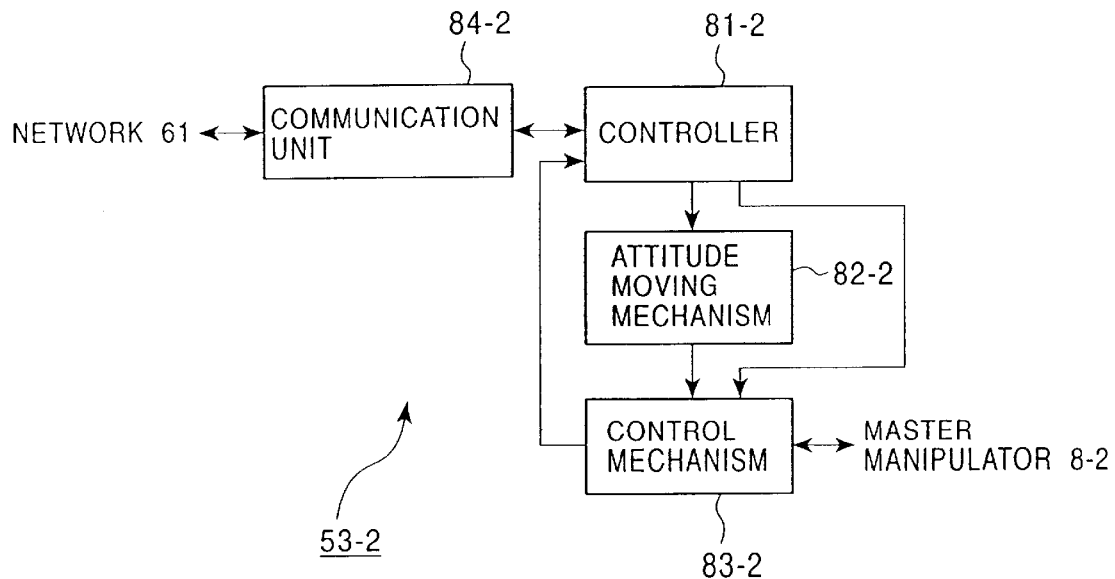
FIG. 10 is a block diagram illustrating an example of the configuration of a master manipulator control unit 53-2 shown in FIG. 7.
Figure 11:
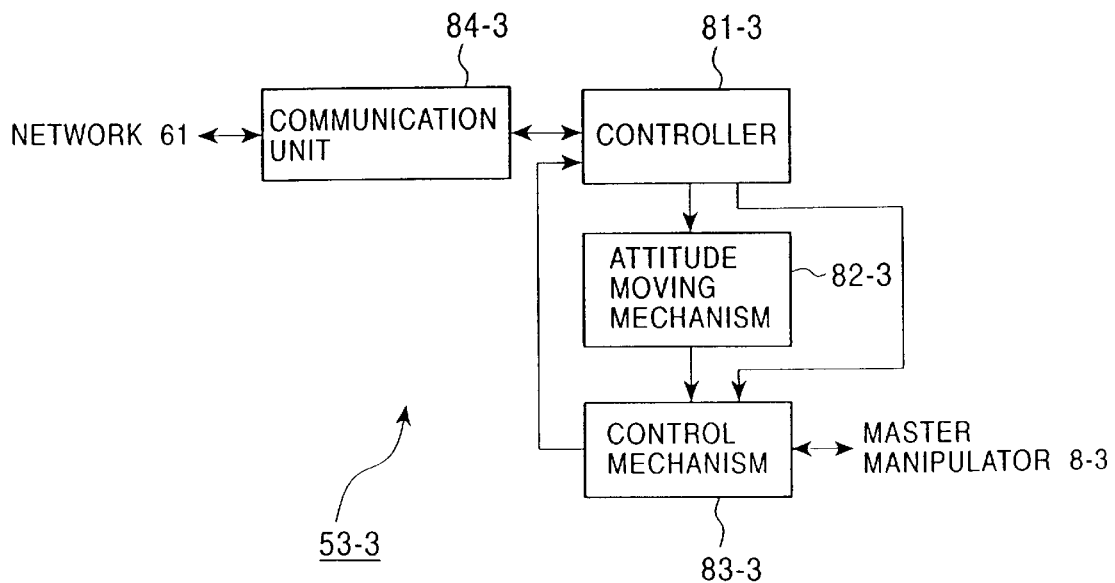
FIG. 11 is a block diagram illustrating an example of the configuration of a master manipulator control unit 53-3 shown in FIG. 7.

FIGS. 10 and 11 illustrate examples of the structures of the master manipulator control units 53-2 and 53-3. The structures there of are similar to the structure of the master manipulator control unit 53-1, and thus they are not described in further detail here.

Referring again to FIG. 7, the input/output controller 54-1 supplies, to the monitor 10-1, the image data supplied from the camera controller 52 via the network 61 or the image data supplied from the master manipulator control unit 53-1. The monitor 10-1 displays an image in accordance with the supplied image data. The input/output controller 54-1 supplies, to the speaker 31-1, the sound/voice data received from the master manipulator control unit 53-1, and the speaker 31-1 outputs a sound/voice in accordance with the supplied sound/voice data.

If the participation switch 33-1 or the synchronization switch 34-1 of the switch unit 32-1 is operated, the input/output controller 54-1 notifies the master manipulator control units 53-1 to 53-3 that the participation switch 33-1 or the synchronization switch 34-1 has been operated.

The input/output controllers 54-2 and 54-3 are similar in structure to the input/output controller 54-1 and thus they are not described in further detail.

The operation of the slave manipulator control unit 51 is described below with reference to a flow chart shown in FIG. 12.

In step S1, the salve manipulator controller 51 starts a preparation for remotely controlling the slave manipulator 3. The details of this process are shown in a flow chart depicted in FIG. 13.

Figure 15:
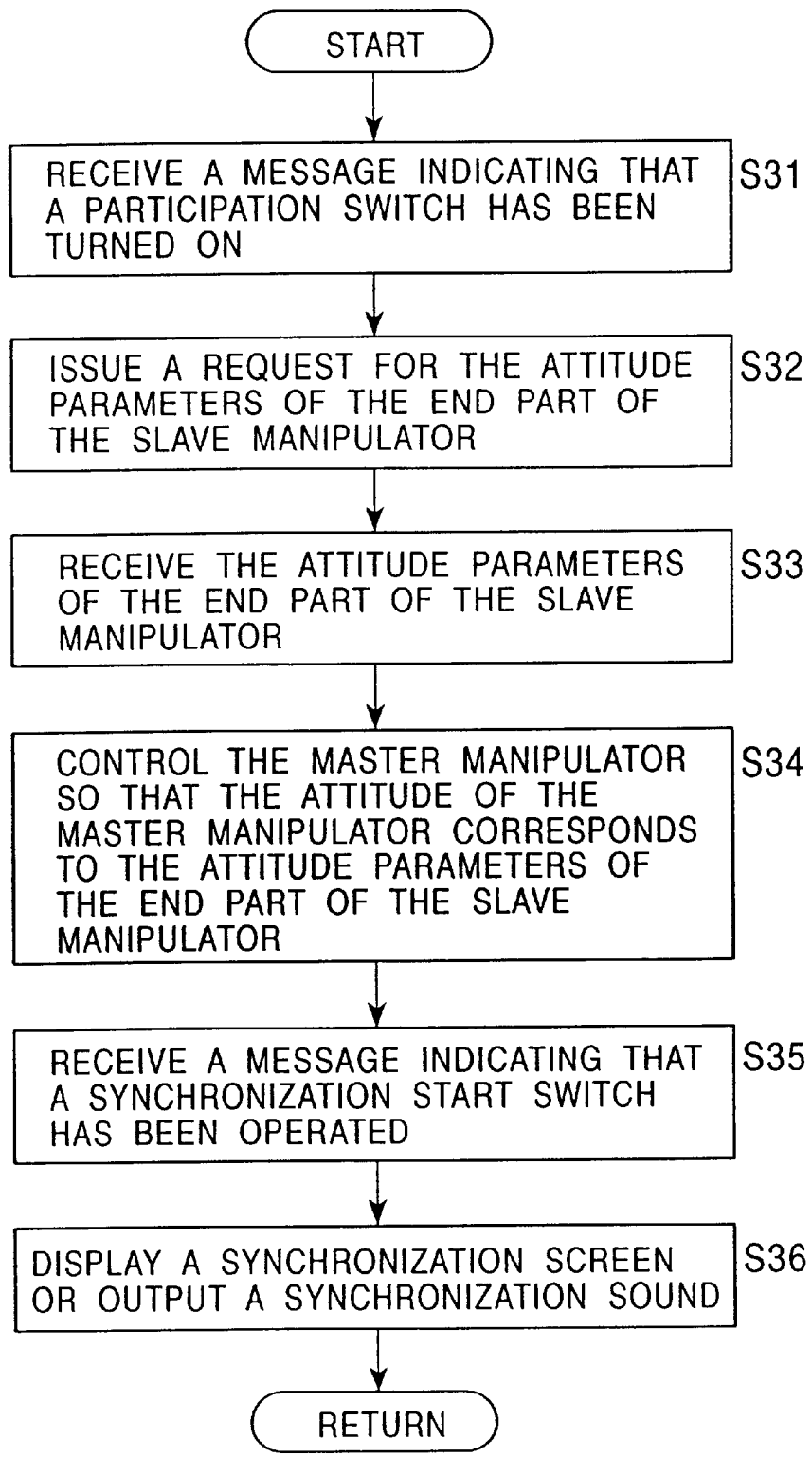
FIG. 15 is a flow chart illustrating the details of step S21 in FIG. 14.

In step S11, the controller 71 of the slave manipulator control unit 51 receives, via the communication unit 74, signals requesting for the attitude parameters of the tip part 4 of the slave manipulator 3, transmitted in step S32, which will be described later with reference to FIG. 15, from the master manipulator control units 53-1 to 53-3.

In step S12, the attitude parameters of the tip part 4 of the slave manipulator 3 are transmitted over the network 61.

The control mechanism 73 of the slave manipulator control unit 51 detects the attitude parameters of the tip part 4 of the slave manipulator 3 and supplies the detected attitude parameters to the controller 71. The controller 71 transmits, via the communication unit 74, the attitude parameters received from the control mechanism 73 over the network 61.

Figure 2A:
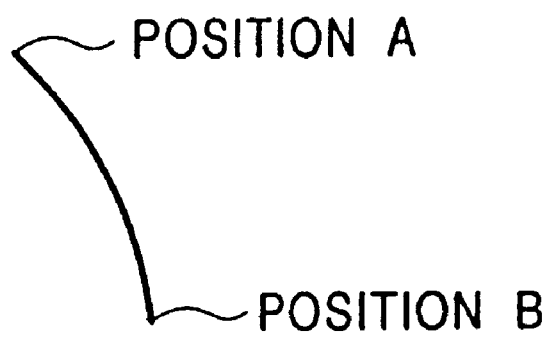
FIGS. 2A and 2B are diagrams illustrating the motion of a tip part of a slave manipulator.
Figure 2B:
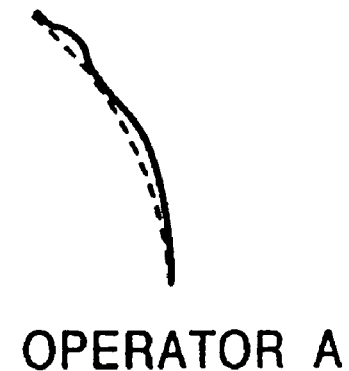

After completion of the above preparative step, the process proceeds to step S2 shown in FIG. 2.

In step S2, the controller 71 of the slave manipulator control unit 51 acquires, via the communication unit 74, the attitude parameters of the handling parts 9-1 to 9-3 of the master manipulators 8-1 to 8-3, which were transmitted in step S22, which will be described later with reference to FIG. 14, over the network 61 from the master manipulator control units 53-1 to 53-3.

In step S3, The controller 71 calculates the weighted sums of the attitude parameters, acquired in step S2, of the handling parts 9-1 to 9-3 of the master manipulators 8-1 to 8-3, using an equal weighting factor of ⅓.

That is, the coordinates indicating the positions (operating point) of the respective handling parts 9-1 to 9-3 are calculated.

In step S4, the controller 71 transmits the attitude parameters, obtained as the result of the calculation of the weighted sums in step S3, over the network 61 via the communication unit 74.

Thereafter, in step S5, the slave manipulator 3 is controlled such that the tip part 4 has an attitude corresponding to the attitude parameters obtained as the result of the calculation of the weighted sums in step S3

More specifically, the controller 71 of the slave manipulator control unit 51 supplies the attitude parameters obtained in step S3 as the result of the weighted sum to the attitude changing mechanism 72. The attitude changing mechanism 72 produces attitude change information used to move the tip part 4 of the slave manipulator 3 from its current attitude to an attitude specified by the attitude parameters supplied from the controller 71, and supplies the produced attitude change information to the control mechanism 73.

In accordance with the attitude change information received from the attitude changing mechanism 72, the control mechanism 73 produces a control signal and transmits it to the driving unit 23 of the slave manipulator 3. The driving unit 23 drives the arm 22 in accordance with the control signal. As a result, the tip part 4 is moved until the tip part is brought into the attitude corresponding to the attitude parameters obtained as the result of the weighted sum calculated in step S3.

In step S6, data indicating a force F1 and a torque T1, which are applied to the tip part 4 from the outside (from an object in the abdominal cavity of the patient 2) when the attitude of the tip part 4 of the slave manipulator 3 is changed in step S5, is transmitted over the network 61.

More specifically, the control mechanism 73 of the slave manipulator control unit 51 acquires the data indicating the force F1 and the torque T1 applied to the tip part 4 of the slave manipulator 3 and supplies the acquired data to the controller 71. The controller 71 transmits the supplied data indicating the force F1 and the torque T1 over the network 61 via the communication unit 74.

Thereafter, the process returns to step S2 to repeat the steps described above.

In step S3 described above, the attitude parameters of the handling parts 9-1 to 9-3 of the master manipulators 8-1 to 8-3 are acquired in step S2 and the weighted sum thereof is calculated, in step S3, using an equal weighting factor of ⅓ thereby obtaining the mean value thereof. Instead, a greater weighting factor may be employed for attitude parameters of a handling part 9 of a master manipulator 8 that is operated by a highly skilled operator, a smaller weighting factor may be employed for attitude parameters of a handling part 9 of a master manipulator that is operated by a low-skill operator.

The operations of the master manipulator control units 53-1 to 53-3 are described below with reference to a flow chart shown in FIG. 14.

In step S21, the master manipulator control units 53-1 to 53-3 make preparations for remote control of the slave manipulator 3. The details of the preparations are shown in a flow chart depicted in FIG. 15.

In step S31, each of the master manipulator control units 53-1 to 53-3 receives, from the corresponding one of the input/output controllers 54-1 to 54-3, a message indicating that the corresponding one of the participation switches 33-1 to 33-3 of the switch units 32-1 to 32-3 have been operated.

In this example, the operator A operates the participation switch 33-1, the operator B operates the participation switch 33-2, and the operator C operates the participation switch 33-3. In response, the input/output controller 54-1 informs the master manipulator control unit 53-1 that the participation switch 33-1 has been operated, the input/output controller 54-2 informs the master manipulator control unit 53-2 that the participation switch 33-2 has been operated, and the input/output controller 54-3 informs the master manipulator control unit 53-3 that the participation switch 33-3 has been operated.

Thereafter, in step S32, the controllers 81-1 to 81-3 of the respective master manipulator control units 53-1 to 53-3 transmit a request signal to the slave manipulator control unit 51 via corresponding communication units 84-1 to 84-3 to request it to provide the attitude parameters of the tip part 4 of the slave manipulator 3. The slave manipulator control unit 51 receives the request signal (step S11 in FIG. 13).

Figure 13:
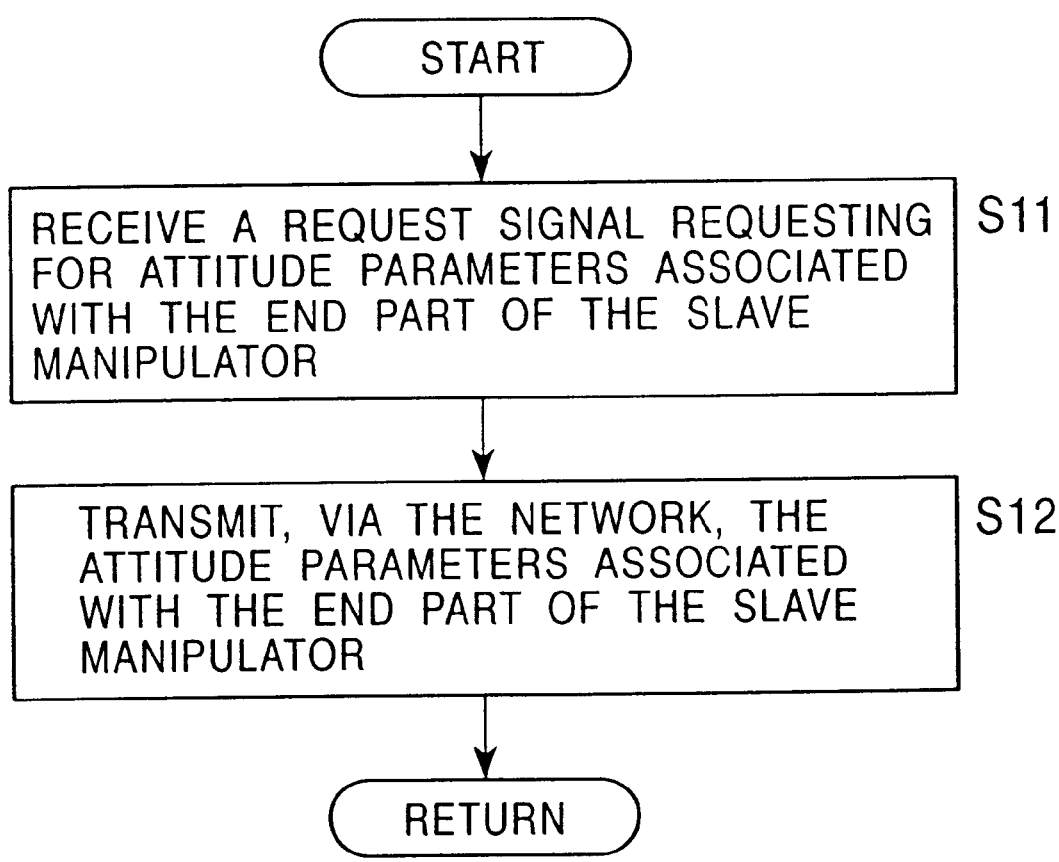
FIG. 13 a flow chart illustrating the details of step S1 in FIG. 12.

In step S33, the controllers 81-1 to 81-3 of the respective master manipulator control units 53-1 to 53-3 receive, via the corresponding communication units 84-1 to 84-3, the attitude parameters of the tip part 4 of the slave manipulator 3, which were transmitted, in step S12 shown in FIG. 13, over the network 61 from the slave manipulator control unit 51.

In step S34, the attitudes of the handling parts 9-1 to 9-3 of the master manipulators 8-1 to 8-3 are controlled such that the attitudes correspond to the attitude parameters (of the tip part 4 of the slave manipulator 3) acquired in step S33.

More specifically, each of the controllers 81-1 to 81-3 of the respective master manipulator control units 53-1 to 53-3 converts the attitude parameters acquired in step S33 into attitude parameters corresponding to the respective spaces associated with the master manipulators 8 and supplies the converted attitude parameters to the corresponding attitude changing mechanisms 82-1 to 82-3. The attitude changing mechanisms 82-1 to 82-3 produce attitude change information used to move the handling parts 9-1 to 9-3 of the respective master manipulators 8-1 to 8-3 from their current attitudes to attitudes specified by the attitude parameters supplied from the controllers 81-1 to 81-3, and supply the produced attitude change information to the control mechanisms 83-1 to 83-3.

In accordance with the attitude change information received from the attitude changing mechanisms 82-1 to 82-3, the control mechanisms 83-1 to 83-3 produce control signals and transmit them to the driving units 43-1 to 43-3 of the master manipulators 8-1 to 8-3. The driving units 43-1 to 43-3 drive the respective arms 42-1 to 42-3 in accordance with the control signals so that the handling parts 9-1 to 9-3 are brought into attitudes corresponding to the attitude parameters of the tip part 4 of the slave manipulator 3 acquired in step S33.

Then, in step S35, the master manipulator control units 53-1 to 53-3 receive, from the input/output controller 54, a message indicating that the synchronization switch 34 of the switch unit 32 has been operated.

More specifically, in this example, the operator A operates the synchronization switch 34-1 of the switch unit 32-1, the input/output controller 54-1 informs the master manipulator control units 53-1 to 53-3 that the synchronization switch 34-1 has been operated. In other words, the master manipulator control units 53-1 to 53-3 receive a message indicating that the synchronization switch 34-1 has been operated.

If the master manipulator control units 53-1 to 53-3 are informed that the synchronization switch 34-1 has been operated, a synchronization screen is displayed, in step S36, on each of the monitors 10-1 to 10-3.

In this example, as shown in FIG. 16, the value of a counter A is decremented every second starting from an initial value of 3 shown in (A) of FIG. 16 until the value reaches a final value of 0 shown in (D), or as shown in FIG. 17 the level (represented by a shaded area in FIG. 17) of a counting indicator B is reduced every second starting from the maximum level ((A) in FIG. 17) until the level reaches the minimum level ((D) in FIG. 17). In any case, the counter value or the counting indicator level is displayed synchronously on all monitors 10-1 to 10-3.

Instead of displaying the synchronization screen on the monitor 10, a synchronization sound may be outputted from the speaker 31 such that, for example, a long sound is outputted after outputting a short sound three times.

Figure 16A:
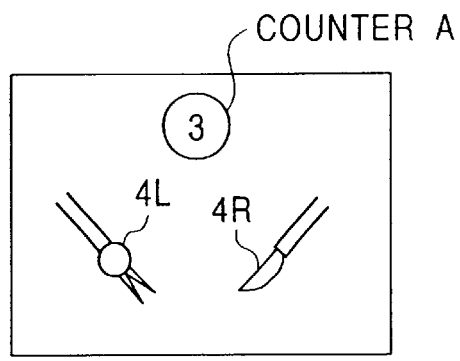
FIGS. 16(A–D) are diagrams illustrating a synchronization screen.
Figure 16B:
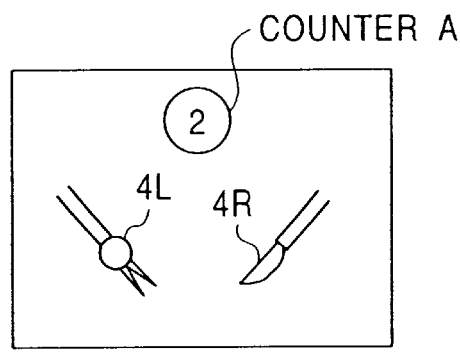
Figure 16C:
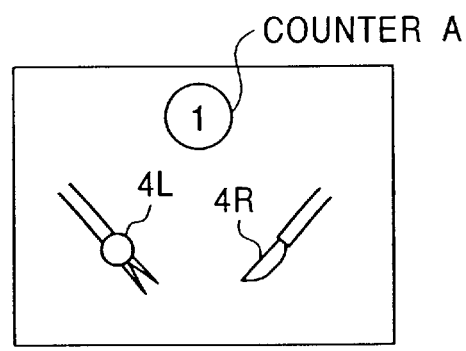
Figure 16D:
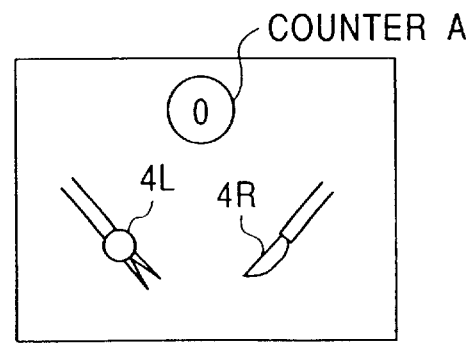
Figure 17A:
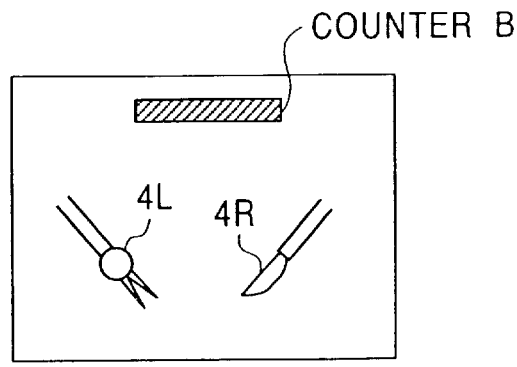
FIGS. 17(A–D) diagrams illustrating another synchronization screen.
Figure 17B:
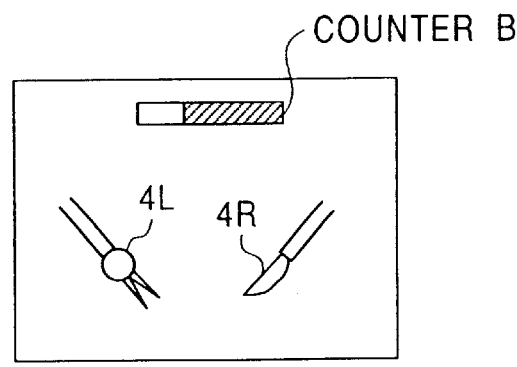
Figure 17C:
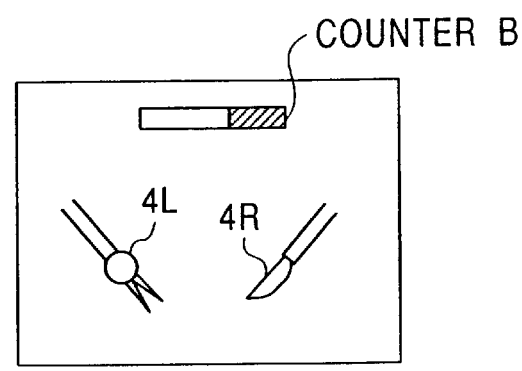
Figure 17D:
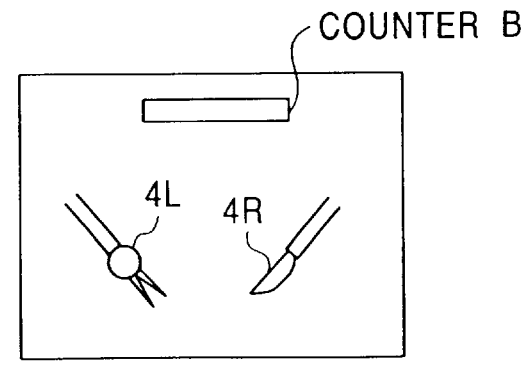

That is, the operators A to C starts to operate the handling parts 9-1 to 9-3 of the master manipulators 8-1 to 8-3 in synchronization with the visual cue shown in FIG. 16(D) or 17(D) indicated on the synchronization screen shown or in synchronization with the long sound/voice cue outputted from the speakers 31-1 to 31-3.

Figure 14:
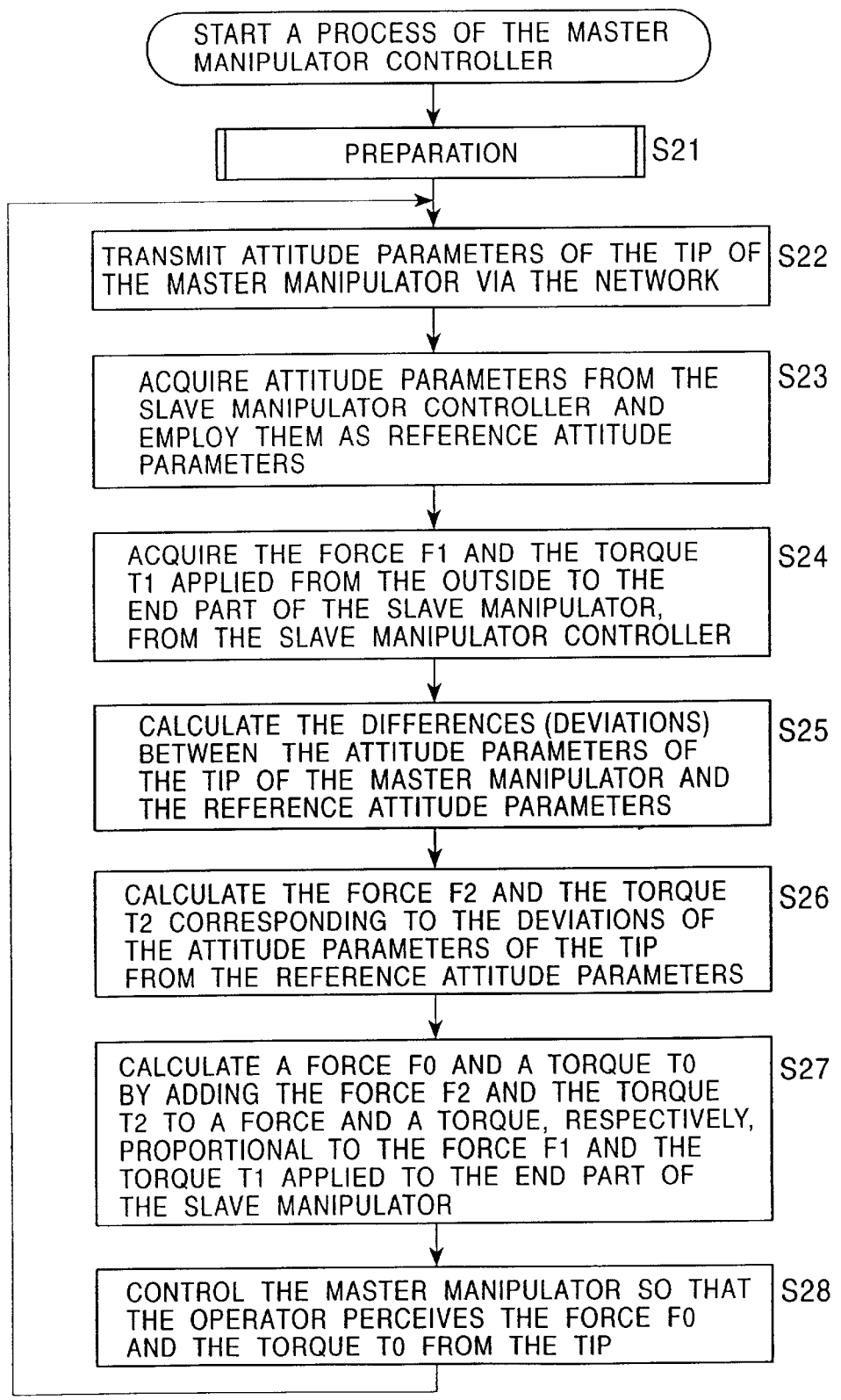
FIG. 14 is a flow chart illustrating the operation of the master manipulator control unit 53.

After completing the preparative process described above, the process associated with the master manipulator control units 53-1 to 53-3 proceeds to step S22 shown in FIG. 14.

In step S22, the attitude parameters of the handling parts 9-1 to 9-3 of the master manipulators 8-1 to 8-3 are transmitted over the network 61.

More specifically, the control mechanisms 83-1 to 83-3 of the respective master manipulator control units 53-1 to 53-3 acquire the attitude parameters of the handling parts 9-1 to 9-3 of the corresponding master manipulators 8-1 to 8-3 and supply them to the controllers 81-1 to 81-3.

The controller 81-1 to 81-3 transmits, via the corresponding communication units 84-1 to 84-3, the attitude parameters supplied from the control mechanisms 83-1 to 83-3 over the network 61.

Figure 12:
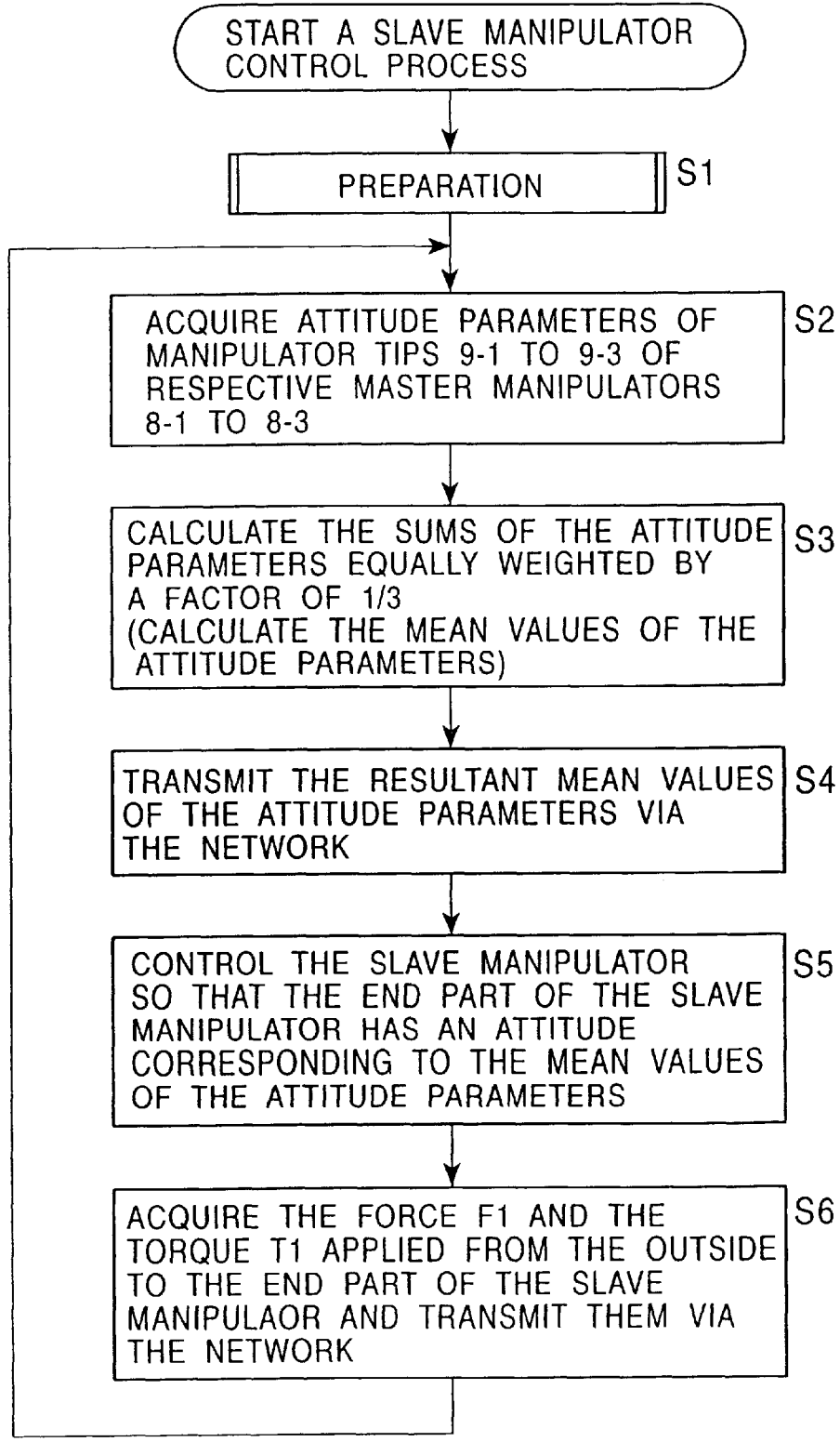
FIG. 12 is a flow chart illustrating the operation of the slave manipulator control unit 51.

The attitude parameters of the handling parts 9-1 to 9-3 transmitted over the network 61 are acquired by the slave manipulator control unit 51 (step S2 in FIG. 12).

In step S23, the controllers 81-1 to 81-3 of the master manipulator control units 53-1 to 53-3 acquire, via the corresponding communication units 84-1 to 84-3, the reference attitude parameters (of the tip part 4 of the slave manipulator 3) that were transmitted in step S4 shown in FIG. 12 over the network 61 from the slave manipulator control unit 51 after calculating the weighted sum of the attitude parameters (of the handling part 9-1 to 9-3 of the master manipulators 8-1 to 8-3) transmitted in step S22.

In step S24, the controllers 81-1 to 81-3 receive, via the corresponding communication units 84-1 to 84-3, the data indicating the force F1 and the torque T1 applied to the tip part 4 of the slave manipulator 3, which was transmitted, in step S6 shown in FIG. 12, from the slave manipulator control unit 51 over the network 61.

In step S25, the controllers 81-1 to 81-3 of the respective master manipulator control units 53-1 to 53-3 calculate the differences between the attitude parameters of the corresponding handling parts 9-1 to 9-3 acquired in step S22 and the reference attitude parameters acquired in step S23.

In step 26, the controllers 81-1 to 81-3 of the respective master manipulator control units 53-1 to 53-3 calculate the force F2 and the torque T2 that are proportional in magnitude to the differences (deviations) calculated in step S25 but opposite in direction to the deviations.

In step S27, the controllers 81-1 to 81-3 add a force and a torque proportional to the force F1 and the torque T1 acquired in step S24 to the respective force F2 and the torque T2 calculated in step S26 thereby determining the force Fo and the torque To to be perceived by the operators A to C operating the handling parts 9-1 to 9-3. More specifically, the force Fo and the torque To are calculated in equation (1) described below.

$$Fo = F2 + \alpha F1$$
$$To = T2 + \beta T1 \qquad (1)$$

In the case where a greater force is needed to move the handling part 9 of the master manipulator 8 than is needed to move the tip part 4 of the slave manipulator 3 (that is, in the case where the handling part 9 is more massive than the tip part 4), $\alpha$ and $\beta$ have values greater than 1. Conversely, if the handling part 9 can be moved by a smaller force than a force needed to move the tip part 4 (that is, in the case where the handling part 9 is less massive than the tip part 4), $\alpha$ and $\beta$ have values smaller than 1. In the case where the handling part 9 and the tip part 4 can be moved by an equal force, $\alpha$ and $\beta$ become equal to 1.

In step S28, the master manipulators 8-1 to 8-3 are controlled such that the force Fo and the torque To calculated in the step S27 are perceived by the operators A to C operating the respective handling parts 9-1 to 9-3 of the master manipulators 8-1 to 8-3.

As described above, the force Fo and the torque To perceived by the operators A to C are given by the sum of the force F2 and the torque T2, calculated in step S25 so as to be proportional in magnitude to the deviations and opposite in direction to the deviations and a force and a torque proportional to the force F1 and the torque T1 applied to the tip part 4 of the slave manipulator 3, and thus the operators A to C can perceive both the deviations of the attitude parameters of the handling parts 9-1 to 9-3 from the reference attitude parameters and the force and the torque applied to the tip part 4 of the salve manipulator 3 from the object (in the abdominal cavity of the patient 2) being processed. Alternatively, the force Fo and the torque To may be determined such that the operator perceives only the force F2 and the T2 or only a force and a torque proportional to the force F1 and the torque T1. Instead, only the force Fo or the torque To may be given such that the operator perceives only the force or the torque.

Thereafter, the process returns to step S22 and the steps described above are repeated.

In the above description, the operation of the slave manipulator control unit 51 is described separately from the operations of the master manipulator control units 53-1 to 53-3 with reference to different flow charts (shown in FIGS. 12 and 14). However, in practice, the operations are performed in parallel as shown in a timing chart of FIG. 18.

In FIG. 18, for example, if the master manipulator control units 53-1 to 53-3 transmits, in step S22, the attitude parameters of the handling parts 9-1 to 9-3 of the master manipulators 8-1 to 8-3 over the network 61, the slave manipulator control unit 51 acquires, in step S2, the transmitted attitude parameters. Note that, in FIG. 18, arrows extending to right from blocks of steps S4, S6, and S22 indicate that data produced in those steps is transmitted over the network 61.

Figure 19:
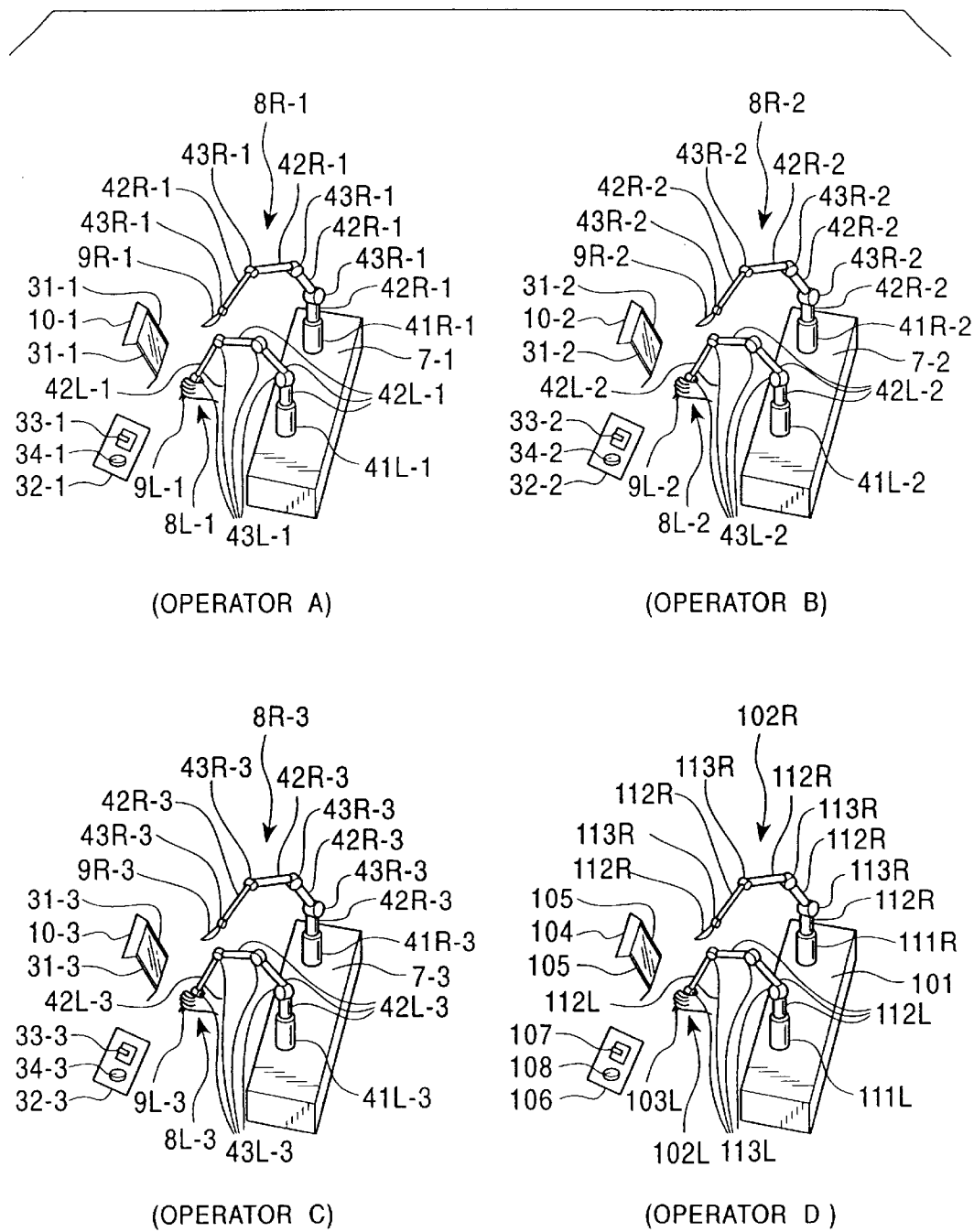
FIG. 19 is a diagram illustrating the outward appearance of another embodiment of a medical operation manipulator system according to the present invention.

FIG. 19 illustrates another example of the configurations of the master manipulator subsystem in the medical operation manipulator system. This master manipulator subsystem is similar to that shown in FIG. 4 except that it further includes, in addition to those parts shown in FIG. 4, a manipulator stage 101, a master manipulator 102 having a handling part 103 disposed on the end thereof, a monitor 104, a speaker 105, and a switch unit 106 including a participation switch 107 and a synchronization switch 108.

A master manipulator 102L is disposed on a base 111L fixed to the manipulator stage 101 and includes a plurality of arms 112L and driving units 113L, which are combined into an articulated structure. A master manipulator 102R is disposed on a base 111R fixed to the manipulator stage 101 and includes a plurality of arms 112R and driving units 113R, which are combined into an articulated structure.

The master manipulators 102 are operated by the operator D. More specifically, the handling part 103L of the master manipulator 102L is handled three-dimensionally by the left hand of the operator D, and the handling part 103R of the master manipulator 102R is handled three-dimensionally by the right hand of the operator D.

An image taken by the CCD camera 6 of the camera unit 5 (FIG. 3) is displayed on the monitor 104.

Figure 20:
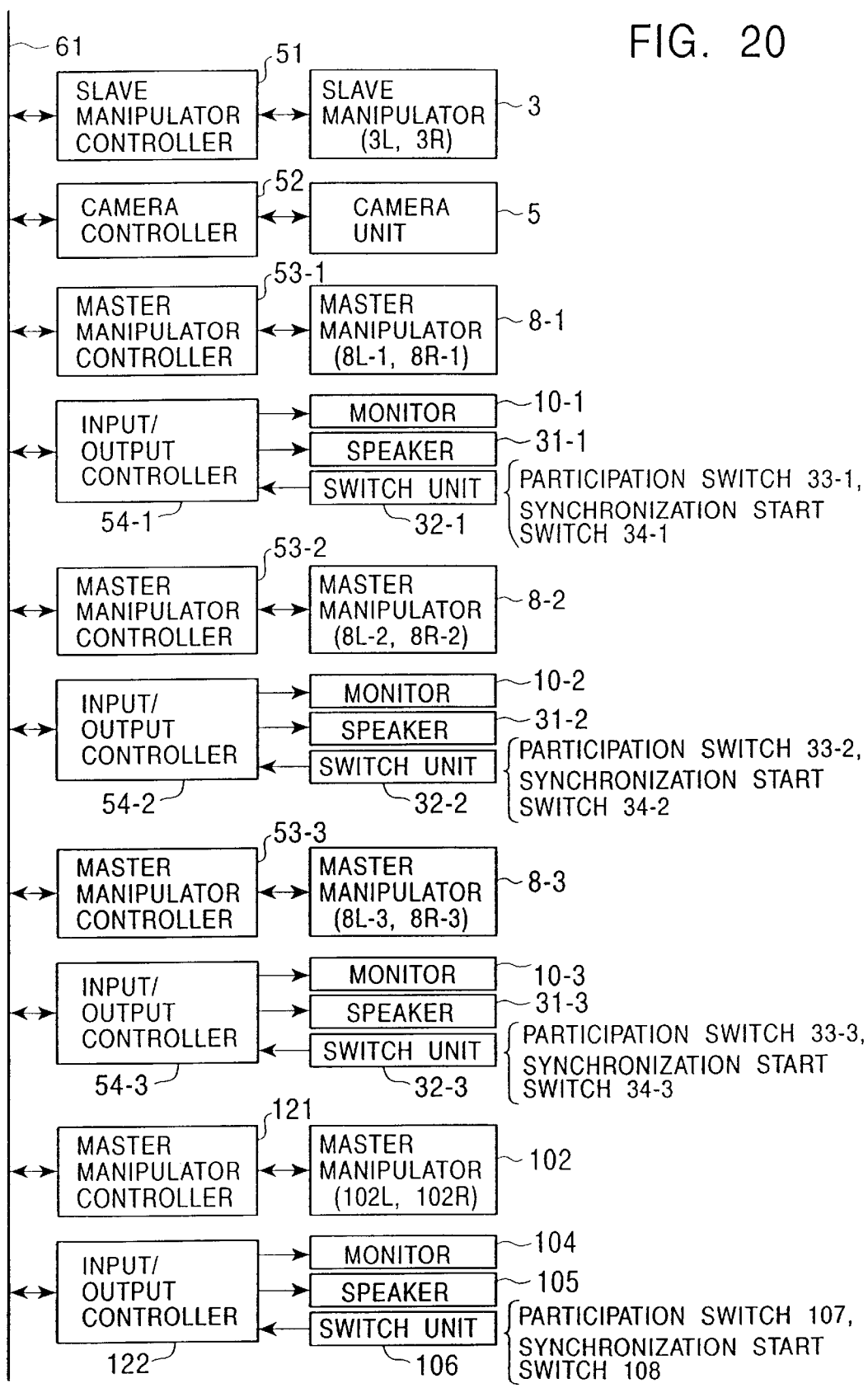
FIG. 20 is a block diagram illustrating another example of the internal configuration of the medical operation manipulator system according to the present invention.

FIG. 20 illustrates an example of the internal structure of the operation manipulator system. In this system, in addition to components in the system shown in FIG. 7, a master manipulator control unit 121 for controlling a master manipulator 102 and an input/output controller 122 for controlling a monitor 104, a speaker 105, and a switch unit 106 are connected to the network 61.

In this system, the slave manipulator control unit 51 acquires attitude parameters of handling parts 9-1 to 9-3 of master manipulators 8-1 to 8-3 transmitted over the network 61 from the master manipulator control units 53-1 to 53-3 and also acquires the attitude parameters (relative attitude parameters that will be described in detail later) of a handling part 103 of the master manipulator 102 transmitted over the network 61 from the master manipulator control unit 121. In accordance with the acquired attitude parameters, the slave manipulator control unit 51 calculates the attitude parameters of the tip part 4 of the slave manipulator 3.

The slave manipulator control unit 51 then controls the slave manipulator 3 such that the tip part 4 of the slave manipulator 3 is brought into an attitude corresponding to the calculated attitude parameters.

Furthermore, the slave manipulator control unit 51 transmits data indicating a force F1 and a torque T1 applied to the tip part 4 of the slave manipulator 3 over the network 61.

In this example, the master manipulator controller 53-1 detects the attitude parameters of the handling part 9-1 of the master manipulator 8-1 and transmits the detected attitude parameters over the network 61.

The master manipulator control unit 53-1 acquires the attitude parameters of the handling parts 9-2 and 9-2 of the respective master manipulators 8-2 and 8-2 transmitted over the network 61 from the master manipulator control units 53-2 and 53-3. The master manipulator control unit 53-1 calculates the mean values of the acquired attitude parameters and the attitude parameters of the handling part 9-1 and employs the resultant mean values as reference attitude parameters. The master manipulator control unit 53-1 then calculates the differences (deviations) between the attitude parameters of the handling part 9-1 and the reference attitude parameters.

The master manipulator control unit 53-1 acquires data indicating the force F1 and the torque T1 transmitted over the network 61 from the slave manipulator control unit 51. In accordance with the acquired force F1 and torque T1 and the calculated differences (deviations), the master manipulator control unit 53-1 calculates the force Fo and the torque To to be perceived by the operator A.

The master manipulator control unit 53-1 then controls the master manipulator 8-1 such that the operator A perceives the force Fo and the torque To.

The master manipulator control units 53-2 and 53-3 function in a similar manner to the master manipulator control unit 53-1, and thus they are not described herein.

In the example shown in FIG. 4, the reference attitude parameters are given by the mean value of the attitude parameters of the handling parts 9-1 to 9-3 of the master manipulators 8-1 to 8-3, and the tip part 4 of the salve manipulator 3 is controlled so as to have an attitude corresponding to the reference attitude parameters, and thus, in this example shown in FIG. 4, the reference attitude parameters are equal to the attitude parameters of the tip part 4.

In contrast, in the example shown in FIG. 19, the attitude of the tip part 4 of the slave manipulator 3 are determined in accordance with the attitude parameters of the handling parts 9-1 to 9-3 of the master manipulators 8-1 to 8-3 and the attitude parameters of the handling part 103 of the master manipulator 102, and thus, in this example shown in FIG. 19, the reference attitude parameters are different from the attitude parameters of the tip part 4.

The master manipulator control unit 121 acquires the attitude parameters of the handling part 103 of the master manipulator 102 and calculates the differences from attitude parameters (starting attitude parameters) for a predetermined attitude (starting attitude). The resultant differences indicate relative attitude of the handling part 103 of the master manipulator with respect to the starting attitude.

The starting attitude of the handling part 103 is selected so that the operator D can easily hold the handling part 103 in the starting attitude. More specifically, for example, the starting attitude of the handling part 103 is selected so as to be as high as the breast of the operator D who operates the master manipulator 102 and who stands between the monitor 104 and the manipulator stage 101 and so as to be properly spaced from the breast of the operator D.

The master manipulator control unit 121 transmits, over the network 61, relative attitude parameters, that is, the calculated differences between the attitude parameters of the handling part 103 of the master manipulator 102 and the starting attitude parameters thereof.

The master manipulator control unit 121 acquires data indicating the force F1 and the torque T1 transmitted over the network 61 from the slave manipulator control unit 51. In accordance with the acquired data indicating the force F1 and the torque T1 and the calculated differences between the attitude parameters of the handling part 103 and the starting attitude parameters, the master manipulator control unit 121 calculates the force Fo and the torque To to be perceived by the operator D.

The master manipulator control unit 121 then controls the master manipulator 102 such that the operator D perceives the force Fo and the torque To.

Figure 21:
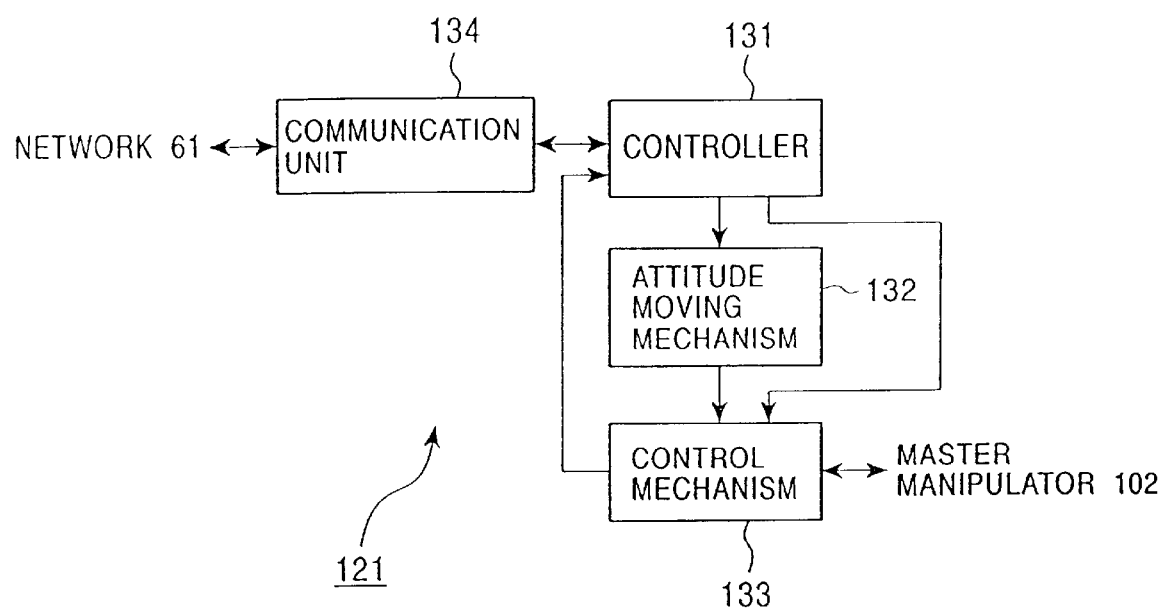
FIG. 21 is a block diagram illustrating an example of the configuration of a manipulator control unit 121 shown in FIG. 20.

FIG. 21 illustrates an example of the configuration of the master manipulator control unit 121.

A controller 131 calculates the differences between the attitude parameters of the handling part 103 of the master manipulator 102 supplied from the control mechanism 133 and the starting attitude parameters stored in a storage unit (not shown) disposed in the controller 131. The calculation result indicating the relative attitude parameters of the handling part 103 is outputted via a communication unit 134.

The controller 131 acquires, via the communication unit 134, data indicating the force F1 and the torque T1 transmitted over the network 61 from the slave manipulator control unit 51. In accordance with the acquired data indicating the force F1 and the torque T1 and the differences between the attitude parameters of the handling part 103 of the master manipulator 102 and the starting attitude parameters thereof, the controller 131 calculates the force Fo and the torque To and supplies data indicating the force Fo and the toque To to a control mechanism 133.

In accordance with the data indicating the force Fo and the toque To supplied from the controller 131, the control mechanism 133 produces a control signal and transmits it to a driving unit 113 of the master manipulator 102. The driving unit 113 drives an arm 112 in accordance with the received control signal such that the handling part 103 of the master manipulator 102 provides the force Fo and the torque To calculated by the controller 131.

The control mechanism 133 detects the attitude parameters of the handling part 103 of the master manipulator 102 and supplies the detected attitude parameters to the controller 131.

Referring again to FIG. 20, the input/output controller 122 receives, via the network 61, image data from the camera controller 52 and supplies the received image data to the monitor 104, which in turn displays an image in accordance with the received image data.

If the participation switch 107 or the synchronization switch 108 of the switch unit 106 is operated, the input/output controller 122 informs the master manipulator control unit 121 that the switch 107 or 108 has been operated.

Now, the operation of the slave manipulator control unit 51 is described with reference to a flow chart shown in FIG.

22, the operations of the master manipulator control units 53-1 to 53-3 are described with reference to a flow chart shown in FIG. 23, and the operation of the slave manipulator control unit 121 is described with reference to flow charts shown in FIGS. 24 and 25, wherein the outlines of the operations are first described, and then specific examples of operations are described, in particular, concerning the operations of the master manipulators 8-1 to 8-3 and 102 by the operators A to D.

First, the operation of the slave manipulator control unit 51 is described with reference to FIG. 22.

In step S61, the master manipulator control unit 51 makes preparations for remote control of the slave manipulator 3. This preparative process in step S61 is performed in a similar manner to step S1 shown in FIG. 12, and thus it is not described in further detail herein.

Figure 23:
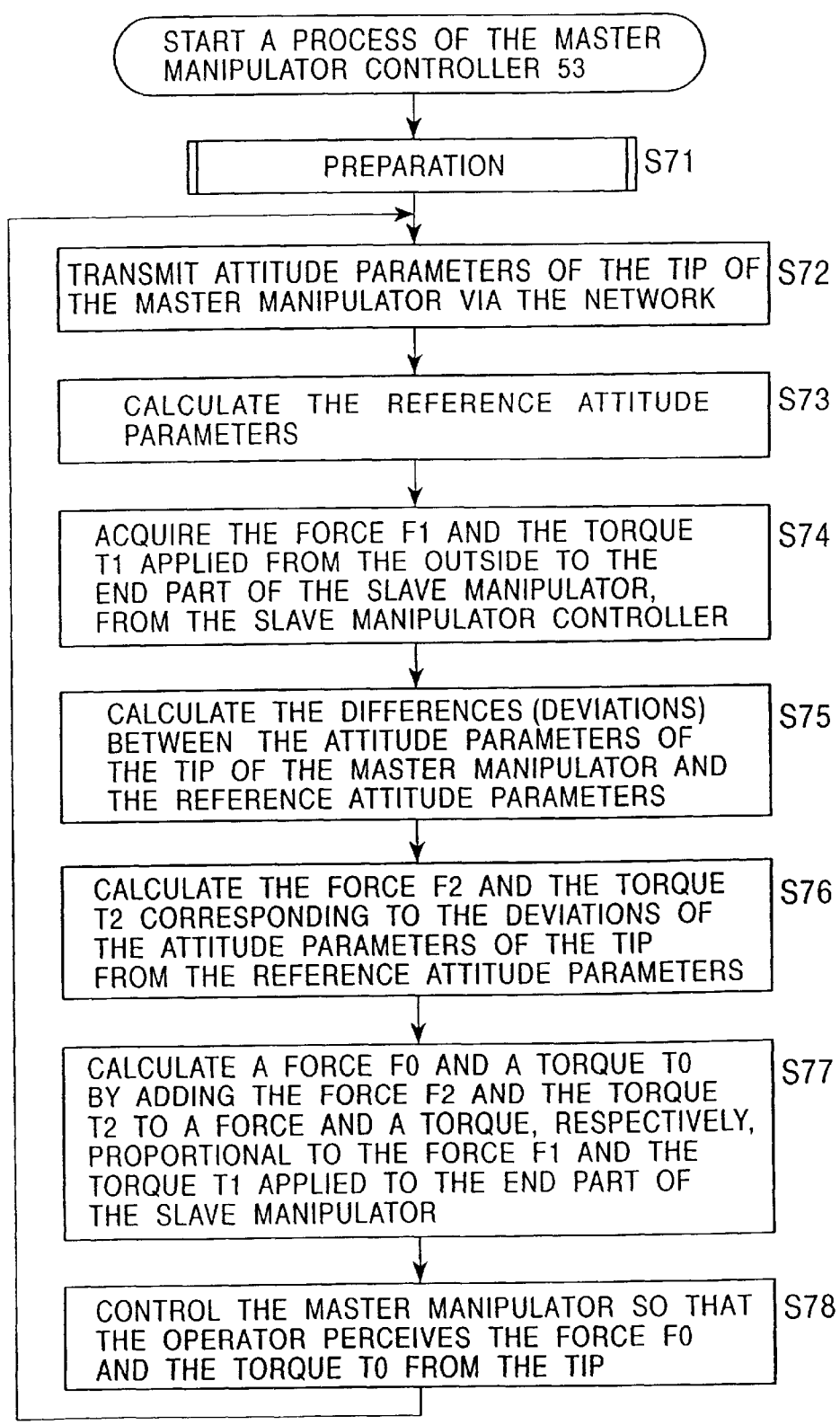
FIG. 23 is a flow chart illustrating another operation of the master manipulator control unit 53.
Figure 24:
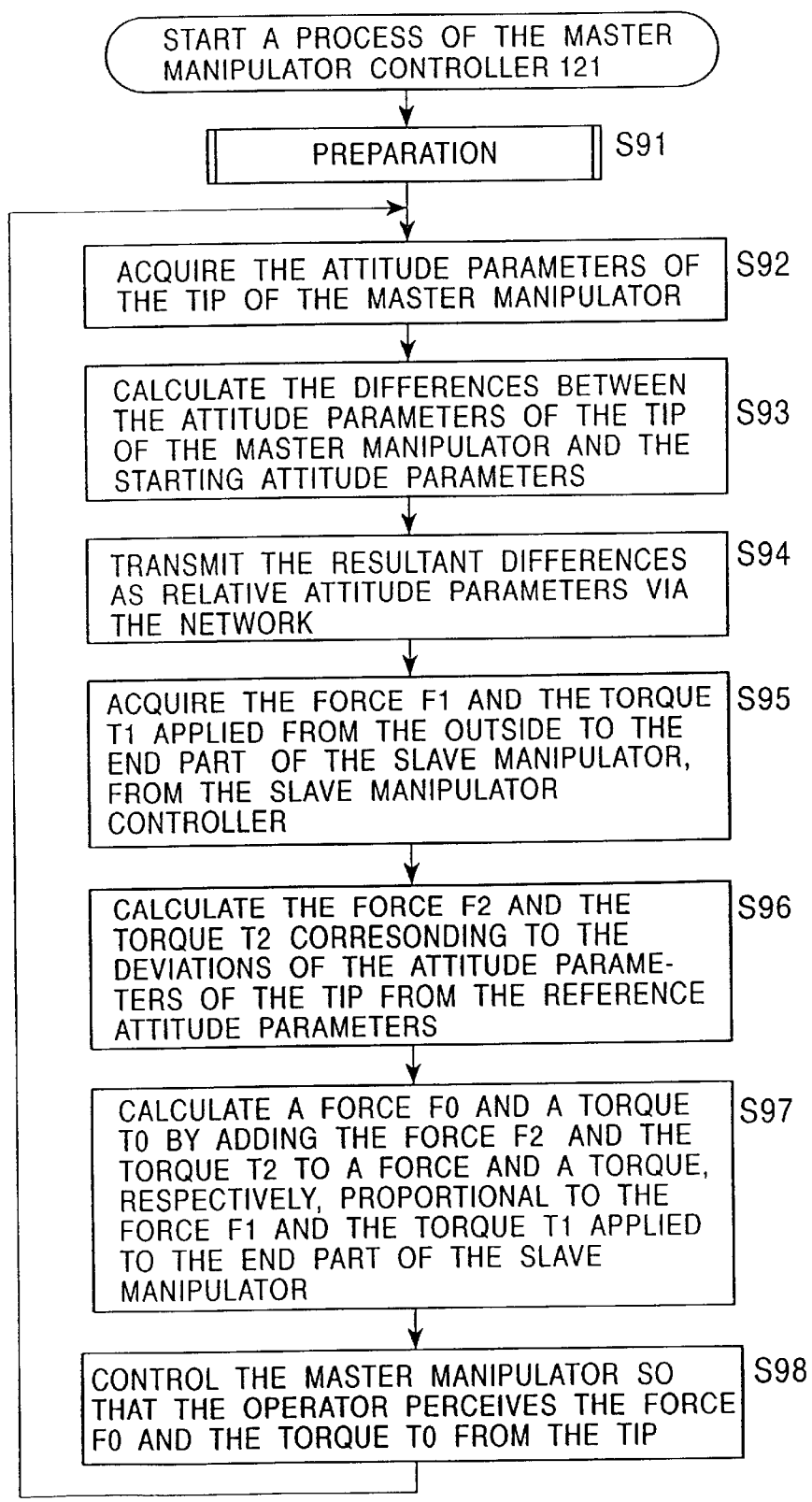
FIG. 24 is a flow chart illustrating the operation of the master manipulator control unit 121.

In step S62, the controller 71 of the slave manipulator control unit 51 acquires, via the communication unit 74, the attitude parameters of the handling parts 9-1 to 9-3 of the master manipulators 8-1 to 8-3 transmitted, in step S72 shown in FIG. 23, over the network 61 from the respective master manipulator control units 53-1 to 53-3 and also acquires the attitude parameters (relative parameters) of the handling part 103 of the master manipulator 102 transmitted, in step S94 shown in FIG. 24, over the network 61 from the master manipulator control unit 121.

In step S63, the controller 71 calculates the weighted sum for the parameters acquired in step S62, that is, the controller 71 calculates the sum of the attitude parameters of the handling parts 9-1 to 9-3 each weighted by a factor of ⅓ and the relative attitude parameters of the handling part 103 weighted by a factor of 1.

Thereafter in step S64, the slave manipulator 3 is controlled such that the slave manipulator 3 has an attitude corresponding to the attitude parameters obtained in step S63 as a result of the calculation of the weighted sum.

This step is performed in a similar manner to above-described step S5 shown in FIG. 12, and thus it is not described in further detail here.

In step S65, data indicating a force F1 and a torque T1, which are applied to the tip part 4 from the outside when the tip part 4 of the slave manipulator 3 is moved, in step S64, into an attitude corresponding to the attitude parameters obtained as the result of the weighted sum calculated in step S63, is transmitted over the network 61.

This step is performed in a similar manner to above-described step S6 shown in FIG. 12, and thus it is not described in further detail here.

Thereafter, the process returns to step S62, and above-described steps are repeated.

Now, the operations of the master manipulator control units 53-1 to 53-3 are described with reference to the flow chart shown in FIG. 23.

In step S71, preparations for remote control of the slave manipulator 3 are made. This step is performed in a similar manner to step S21 shown in FIG. 14, and thus it is not described in further detail herein.

In step S72, the attitude parameters of the handling parts 9-1 to 9-3 of the master manipulators 8-1 to 8-3 are transmitted over the network 61.

This step is performed in a similar manner to step S22 shown in FIG. 14, and thus it is not described in further detail herein.

In step S73, each of the master manipulator control units 53-1 to 53-3 calculates the mean values of the attitude parameters of the handling parts 9-1 to 9-3 of the master manipulators 8-1 to 8-3 and employs the resultant mean values as reference attitude parameters.

More specifically, the controller 81-1 of the master manipulator control unit 53-1 acquires via the communication unit 84-1 the attitude parameters of the handling parts 9-2 and 9-3 of the master manipulators 8-2 and 8-3 transmitted in step S72 over the network 61. The controller 81-1 calculates the weighted sums of the acquired attitude parameters of the handling parts 9-2 and 9-3 and the attitude parameters of the handling part 9-1 of the master manipulator 8-1, using an equal weight factor of ⅓ for all terms, and employs the result as the reference attitude parameters.

The controller 81-2 of the master manipulator control unit 53-2 acquires via the communication unit 84-2 the attitude parameters of the handling parts 9-1 and 9-3 of the master manipulators 8-1 and 8-3 transmitted in step S72 over the network 61. The controller 81-2 calculates the weighted sums of the acquired attitude parameters of the handling parts 9-1 and 9-3 and the attitude parameters of the handling part 9-2 of the master manipulator 8-2, using an equal weight factor of ⅓ for all terms, and employs the result as the reference attitude parameters.

The controller 81-3 of the master manipulator control unit 53-3 acquires via the communication unit 84-3 the attitude parameters of the handling parts 9-1 and 9-2 of the master manipulators 8-1 and 8-2 transmitted in step S72 over the network 61. The controller 81-3 calculates the weighted sums of the acquired attitude parameters of the handling parts 9-1 and 9-2 and the attitude parameters of the handling part 9-3 of the master manipulator 8-3, using an equal weight factor of ⅓ for all terms, and employs the result as the reference attitude parameters.

Figure 22:
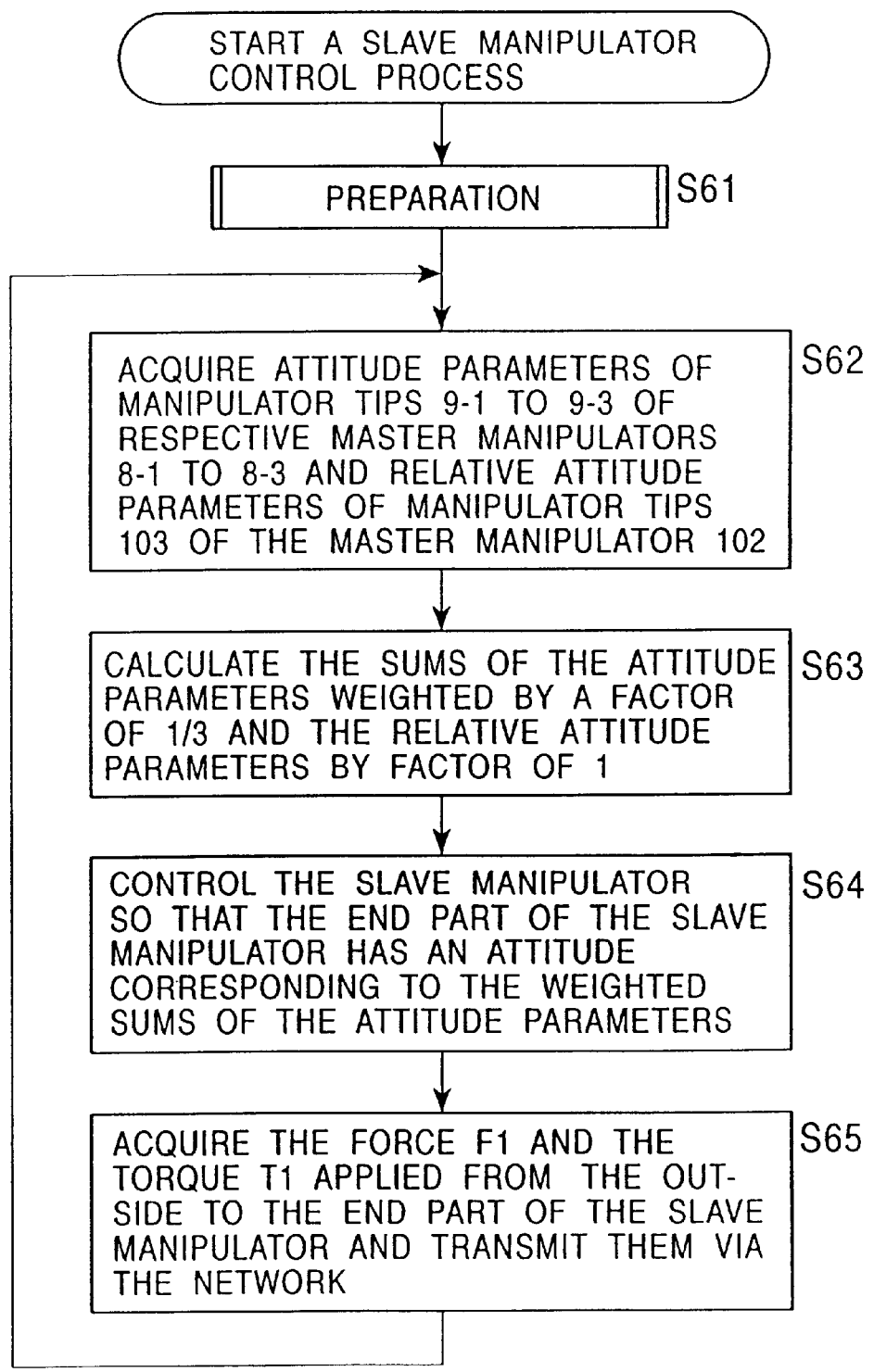
FIG. 22 is a flow chart illustrating another operation of the slave manipulator control unit 51.

Thereafter, in step S74, the controllers 81-1 to 81-3 of the master manipulator control units 53-1 to 53-3 acquire, via their communication units 84-1 to 84-3, data indicating the force F1 and the torque T1 applied to the tip part 4 of the slave manipulator 3 transmitted in step S65 shown in FIG. 22 over the network 61 from the slave manipulator control unit 51.

In step S75, the controllers 81-1 to 81-3 of the master manipulator control units 53-1 to 53-3 calculates the differences between the attitude parameters, of the corresponding handling parts 9-1 to 9-3 of the master manipulators 8-1 to 8-3 acquired in step S72, and the reference parameters calculated in step S73.

In step S76, the controllers 81-1 to 81-3 calculate the force F2 and the torque T2 that are proportional in magnitude to the differences (deviations) calculated in step S75 but opposite in direction to the direction of deviation.

In step S77, the controllers 81-1 to 81-3 add a force and a torque proportional to the force F1 and the torque T1 acquired in step S74 to the force F2 and the torque T2 calculated in step S76 thereby determining the force Fo and the torque To to be perceived by the respective operators A and C operating the handling parts 9-1 to 9-3 of the master manipulators 8-1 to 8-3. More specifically, the force Fo and the torque To are calculated in accordance with equation (1).

In step S78, the master manipulators 8-1 to 8-3 are controlled such that the operators A to C perceive the force Fo and the torque To calculated in step S77.

This step is performed in a similar manner to step S28 shown in FIG. 14, and thus it is not described in further detail herein.

Thereafter, the process returns to step S72, and the steps described above are repeated.

The operation of the master manipulator control unit 121 is described with reference to the flow charts shown in FIGS. 24 and 25.

In step S91, the master manipulator control unit 121 makes preparations for remote control of the slave manipulator 3. The details of this step are shown in the flow chart of FIG. 25.

In step S101, the master manipulator control unit 121 receives from the input/output controller 122 a message indicating that the participation switch 107 of the switch unit 106 has been operated.

More specifically, in this example, the operator D operates the participation switch 107, and the input/output controller 122 informs the master manipulator control unit 121 that the participation switch 107 has been operated.

In step S102, the master manipulator 102 is controlled such that the handling part 103 thereof is brought into its starting attitude.

More specifically, the controller 131 of the master manipulator control unit 121 read the starting attitude parameters stored in a storage unit disposed in the controller 131. The controller 13 supplies the read starting attitude parameters to the attitude changing mechanism 132, The attitude changing mechanism 132 produces attitude change information according to which the handling part 103 of the master manipulator 102 is to be brought from a current attitude into an attitude corresponding to the starting attitude parameters supplied from the controller 131. The produced attitude change information is supplied to the control mechanism 133.

In accordance with the attitude change information received from the attitude changing mechanism 132, the control mechanism 133 produces a control signal and transmits it to the driving unit 113 of the master manipulator 102. In accordance with the control signal, the driving unit 113 drives the arm 112 such that the handling part 103 is brought into the starting attitude.

After completing the preparative process described above, the process associated with the master manipulator control unit 121 proceeds to step s92 shown in FIG. 24.

In step S92, the controller 131 of the master manipulator control unit 121 acquires the attitude parameters of the handling part 103 of the master manipulator 102. In step S93, the controller 131 of the master manipulator control unit 121 calculates the differences between the acquired attitude parameters of the handling part 103 and the starting attitude parameters.

Thereafter, in step S94, the controller 131 transmits, over the network 61 via the communication unit 134, the relative attitude parameters given in step S93 as the differences between the attitude parameters of the handling part 103 and the starting attitude parameters.

In step S95, the controller 131 acquires, via the communication unit 134, data indicating the force F1 and the torque T1 transmitted in step S65 of FIG. 22 over the network 61 from the slave manipulator control unit 51.

In step S96, the controller 131 calculates the force F2 and the torque T2 that are proportional to the magnitudes of the differences (deviations) calculated in step S93 but opposite in direction to the direction of deviation.

In step S97, the controller 131 adds a force and a torque proportional to the force F1 and the torque T1 acquired in step S95 to the respective force F2 and torque T2 calculated in step S96 thereby determining the force Fo and the torque To to be perceived by the operator D. More specifically, the force Fo and the torque To are calculated in accordance with equation (1).

In the case where a greater force is needed to move the handling part 103 of the master manipulator 102 than is needed to move the tip part 4 of the slave manipulator 3 (that is, in the case where the handling part 103 is more massive than the tip part 4), $\alpha$ and $\beta$ have values greater than 1. Conversely, if the handling part 103 can be moved by a smaller force than a force needed to move the tip part 4 (that is, in the case where the handling part 103 is less massive than the tip part 4), $\alpha$ and $\beta$ have values smaller than 1. In the case the handling part 100 and the tip part 4 can be moved by an equal force, $\alpha$ and $\beta$ become equal to 1.

In step S98, the master manipulator 102 is controlled such that the operator D perceives the force Fo and the torque To calculated in step S97.

Thereafter, the process returns to step S92, and above-described steps are repeated.

Figure 26A:
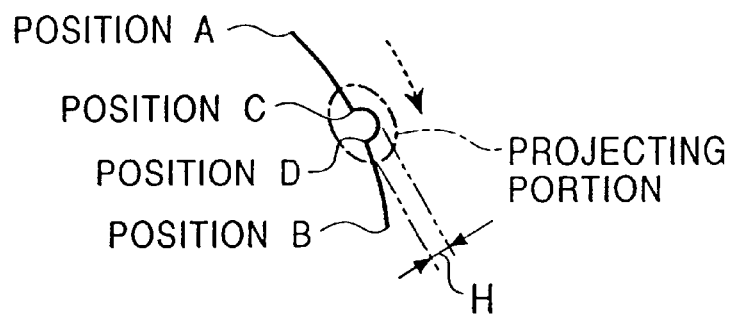
FIGS. 26A to 26C are diagrams illustrating the attitudes of the handling parts of the master manipulator 102.

In a case where the tip part 4 of the slave manipulator 3 is to be moved along a target path including, as shown in FIG. 26A, a curved portion that is located between a position C and a position D and shifted by an amount of H from the main path shown in FIG. 6A, the operators A to D may operate the handling parts 9-1 to 9-3 and the handling part 103 as follows.

Figure 26B:
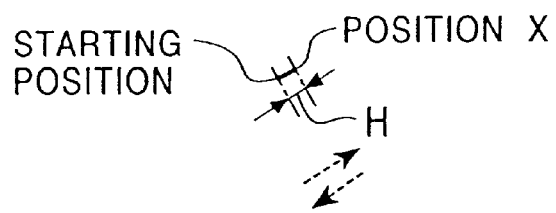

In this case, the operators A to C move the respective master manipulators 8-1 to 8-3 so as to follow the target path shown in FIG. 6A. On the other hand, if the operator D determines that the tip part 4 of the slave manipulator 3 has reached the position C, the operator D shifts the handling part 103 of the master manipulator 102 from the starting attitude (starting position) by an amount corresponding to H (by an amount equal to H, in this specific example) to a position X as shown in FIG. 26B and then shifts the handling part 103 back to the starting attitude (starting position) along the same path as the shift-to-X path. A dotted arrow in FIG. 26A indicates the direction of the target path, and dotted arrows in FIG. 26B indicate directions in which the handling part 103 are moved.

If the handling part 103 of the master manipulator 102 is not moved after setting its attitude into the starting attitude in the preparative step S91 shown in FIG. 24, then the attitude parameters of the handling part 103 are maintained in the starting attitude parameters, and thus the differences from the starting attitude parameters become zero.

Because the attitude parameters that determine (in step S64 in FIG. 22) the attitude of the tip part 4 of the slave manipulator 3 are given (in step S63) by the sum of the attitude parameters, weighted by a factor of ⅓, of the handling parts 9-1 to 9-3 of the respective master manipulators 8-1 to 8-3 and the relative attitude parameters, weighted by a factor of 1, of the handling part 103 of the master manipulator 102, if only the handling parts 9-1 and 9-3 are moved by the respective operators A to C but the handling part 103 is not moved by the operator D (that is, the relative attitude parameters are maintained in zeros), then the tip part 4 of the slave manipulator 3 moves in response only to the motion of the handling parts 9-1 to 9-3.

The operator D monitors the motion of the tip part 4 of the slave manipulator 3 displayed on the monitor 104. If the operator D determines that the tip part 4 has reached the position C after being moved in response to the motion of the handling parts 9-1 to 9-3, the operator D shifts the handling part 103 of the master manipulator 102 by a distance of H from the starting attitude (starting position) to the position X and shifts it back to the original position along the same path.

If the handling part 103 of the master manipulator 102 is shifted from its starting attitude (starting position), the deviations of its attitude parameters (the magnitude of the deviation and the direction thereof) are calculated (in step S93) and the calculation result is transmitted as the relative attitude parameters over the network 61 (step S94).

As a result, the tip part 4 of the slave manipulator 3 is moved in accordance with the motion of the handling parts 9-1 to 9-1 and the handling part 103, and thus the tip part 4 is moved along the curved path.

If the operator D determines, on the basis of the image displayed on the monitor 104, that the tip part 4 of the slave manipulator 3 has reached the position D after moving along the curved path, the operator D stops the operation of the handling part 103 of the master manipulator 102. As a result, the handling part 103 is again brought into the starting attitude (starting position) and maintained therein. That is, the relative attitude parameters become zeros. Therefore, the motion of the tip part 4 of the salve manipulator 3 that occurs thereafter is determined only by the motion of the handling parts 9-1 and 9-3, and thus the tip part 4 is moved to the position B.

Figure 26C:

Thus, as descried above, the tip part 4 of the slave manipulator 3 can be moved along a path very close to the target path, as shown in FIG. 26C.

Another example of the operation of the master manipulator control unit s 53-1 to 53-3 for the subsystem shown in FIG. 19 is described below with reference to a flow chart shown in FIG. 27.

Steps S111 to S116 are performed in a similar manner to steps S71 to S76 shown in FIG. 23, and thus they are not described in further detail herein.

In step S117, the controllers 81-1 to 81-3 of the master manipulator control units 53-1 to 53-3 acquire, via the corresponding communication units 84-1 to 84-3, the relative attitude parameters transmitted in step S134, which will be described later with reference to FIG. 28, over the network 61 from the master manipulator control unit 121.

In step S118, the controllers 81-1 to 81-3 of the master manipulator control units 53-1 to 53-3 determine whether a value (deviation value) corresponding to the relative attitude parameters acquired in step S117 is smaller than a predetermined threshold value T. If the value is determined to be smaller than the predetermined threshold value T, the process proceeds to step S119.

Herein, the deviation value is given by the following equation:

Deviation value=

$$\text{Deviation value} = \sqrt{\sum_{i=1}^{n} W_i P_i^2}$$

where n denotes the number of attitude parameters, $P_i$ denotes the difference associated with each attitude parameter, and $W_i$ denotes the weighting factor applied to $P_i$.

In this case, the attitude parameters include a total of six values, that is, three values of X, Y, and Z coordinates indicating the position and three values of $\theta y$, $\theta p$, and $\theta r$ indicating the state, and thus n=6 and $P_1$ to $P_6$ respectively indicate the differences between the current values of X, Y, and Z coordinates and $\theta y$, $\theta p$, and $\theta r$ of the attitude parameters of the handling part 103 and the corresponding values of the starting attitude parameters. $W_1$ to $W_6$ respectively indicate the predetermined weighting factors for $P_1$ to $P_6$.

In steps S119 and S120, which are performed in a similar manner to steps S77 and S78 shown in FIG. 23 and thus they are described briefly herein, the force F2 and the torque T2 calculated in step S116 are added to the force F1 and the torque T1 applied from the outside to the tip part 4 of the slave manipulator 3 acquired in step S114 thereby determining the force Fo and the torque To, and the master manipulators 8-1 to 8-3 are controlled so that the operators A to C perceive the calculated force Fo and torque To.

On the other hand, in the case where it is determined in step S118 that the value (deviation value) corresponding to the relative attitude parameters is not smaller than the threshold value T (that is, equal to or greater than the threshold value T) the process proceeds to step S121 in which the master manipulators 8-1 to 8-3 are controlled so that the operators 1 to C perceive the force F2 and the torque T2 calculated in step S116.

After step S120 or S121, the process returns to step S112, and the steps described above are repeated.

Now, another operation of the master manipulator control unit 121 (operation associated with the master manipulator control unit 53) is described below with reference to a flow chart shown in FIG. 28.

Steps S131 to S136 are performed in a similar manner to steps S91 to S96 shown in FIG. 24, and thus they are not described in further detail herein.

In step S137, it is determined whether a value (deviation value) corresponding to the differences, calculated in step S133, between attitude parameters of the handling part 103 of the master manipulator 102 and the starting attitude parameters is equal to or greater than a threshold value T. If the value is determined to be equal to or greater than the threshold value T, the process proceeds to step S138.

In steps S138 and S139, although details of these steps are not described because they are performed in a similar manner to steps S97 and S98 shown in FIG. 24, the force Fo and the torque To are determined by adding the force F2 and the torque T2 calculated in step S136 to the force F1 and the torque T1 applied from the outside to the tip part 4 of the slave manipulator 3 acquired in step S135, and the master manipulator 102 is controlled such that the operator D perceives the force Fo and the torque To calculated.

On the other hand, the process proceeds to step S140 if it is determined in step S137 that the value (deviation value) corresponding to the differences between the attitude parameters of the handling part 103 of the master manipulator 102 and the starting attitude parameters is not equal to or greater than (that is, is smaller than) the threshold value T.

In step S140, the master manipulator 102 is controlled such that the operator D perceives the force F2 and the torque T2 calculated in step S136.

After step S139 or S140, the process returns to step S132, and the steps described above are repeated.

Figure 27:
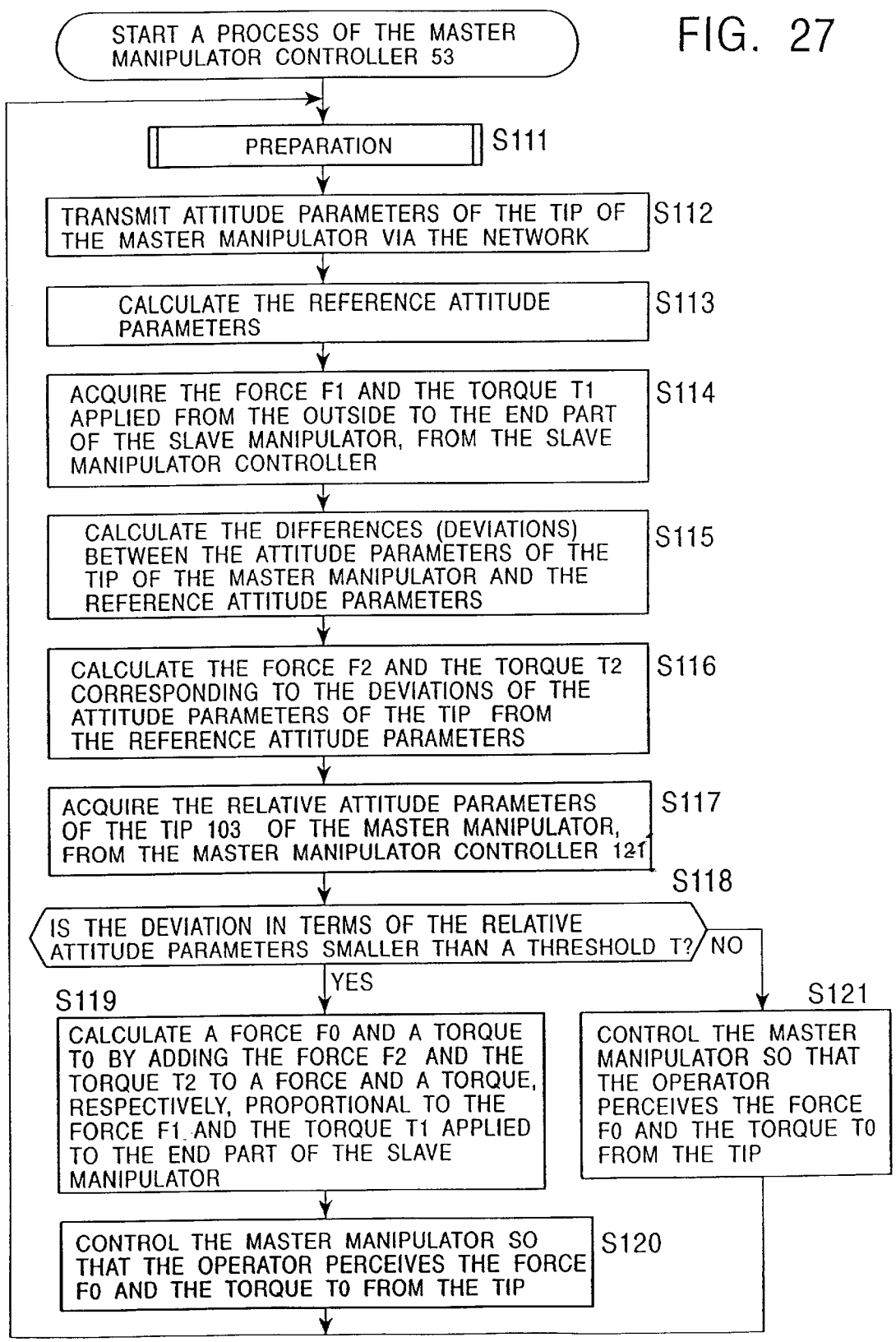
FIG. 27 is a flow chart illustrating another operation of the master manipulator control unit 53.
Figure 28:
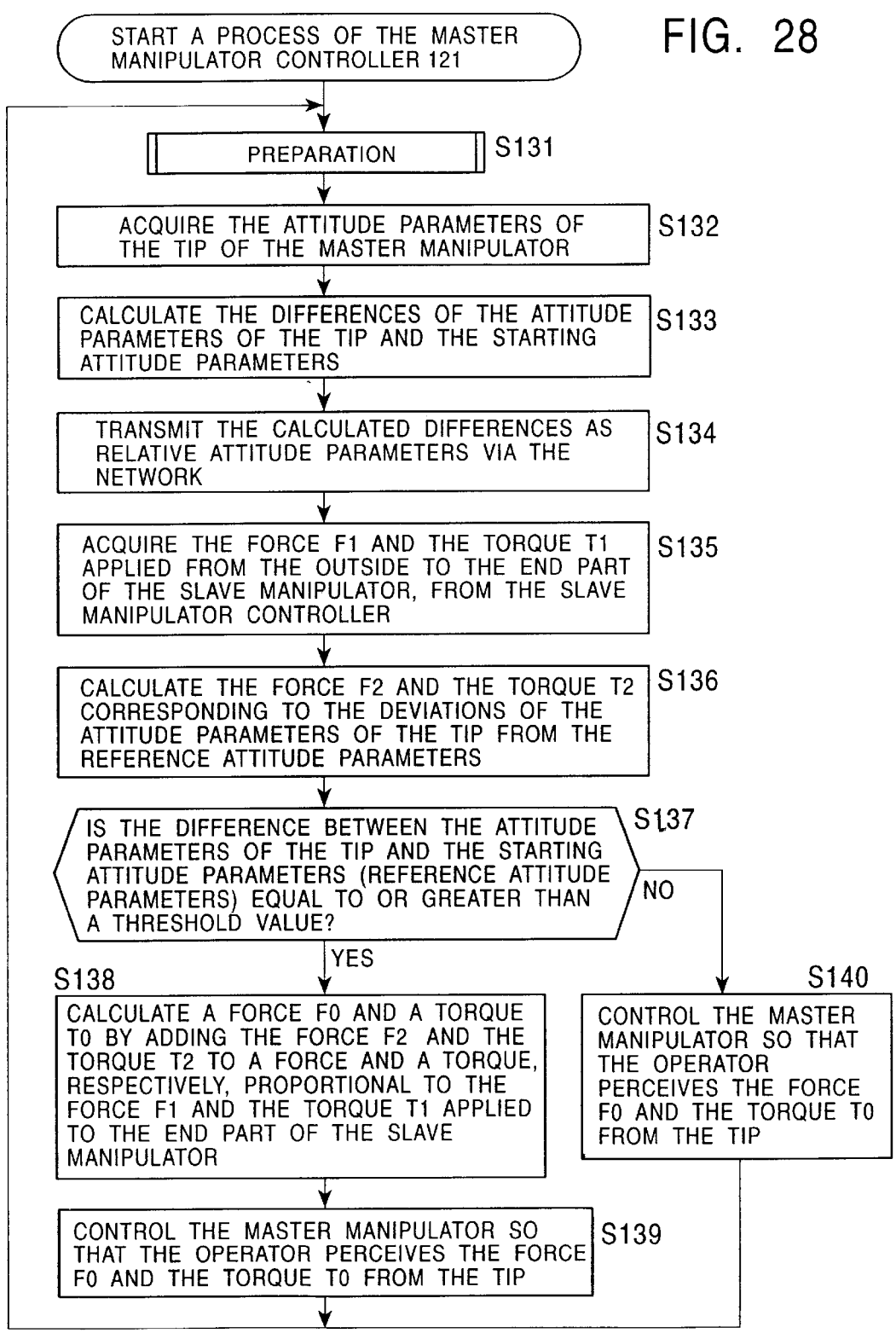
FIG. 28 is a flow chart illustrating another operation of the master manipulator control unit 121.

In the above-described processes shown in the flow charts of FIGS. 27 and 28, if the value (deviation value) corresponding to the relative attitude parameters of the handling part 103 of the master manipulator 102 is determined to be smaller than the threshold value T (step S118 in FIG. 27 or step S137 in FIG. 28), the master manipulators 8-1 to 8-3 are controlled (step S120) such that the operators A to C perceive the force and the torque equal to the sums of the force F2 and the torque T2 calculated in step S116 and the force and the torque applied from the object being treated to the tip part 4 of the slave manipulator 3 (step S120). However, the master manipulator 102 is controlled (step S140) such that the operator D perceives only the force F2 and the torque T2 calculated in step S136 of FIG. 28.

On the other hand, in the case where the value (deviation value) corresponding to the relative attitude parameters of the handling part 103 is equal to or greater than the threshold value T, the master manipulators 8-1 to 8-3 are controlled (step S121 in FIG. 27) such that the operators A to C perceive only the force F2 and the torque T2 calculated in step S116, and the master manipulator 102 is controlled (step S139) such that the operator D perceives the sums of the force F2 and the torque T2 calculated in step S136 of FIG. 28 and the force and the torque applied from the object being treated to the tip part 4 of the slave manipulator 3 (step S138).

Thus, in this specific example, the force and the torque applied from the object being treated to the tip part 4 of the slave manipulator 3 is perceived by the operator D when the tip part 4 is moved along the curved portion of the path and perceived by the operators A to C when the tip part 4 is moved along the other portion of the path.

In the above process (that is, when the process shown in FIGS. 27 and 28 is performed by the master manipulator control unit 53 and the master manipulator control unit 121), the slave manipulator control unit 51 performs the process shown in FIG. 22.

Although the present invention has been described above with reference to the specific embodiments of medical operation manipulator systems, the present invention is not limited to those embodiments. The present invention may also be applied to other types of manipulator systems such as that for use in the outer space or that for use in a danger area.

In the present invention, the steps of the program stored on a storage medium may be performed sequentially in the same order as described in the program or may be performed in parallel or individually.

In the present invention, the term "system" is used to describe the whole of an apparatus including a plurality of sub apparatuses.

As described above, the present invention provides great advantages. That is, in the manipulator system, the method for controlling the manipulator, and the first storage medium in which the program is stored, according to the present invention, the absolute attitude, in the space within which the first handling part is allowed to move, of the first handling part of the first master manipulator is detected, the detected absolute attitude of the first handling part is transmitted, the absolute attitude, in the space within which the second handling part is allowed to move, of the first handling part of the first master manipulator is detected, the detected absolute attitude of the second handling part is transmitted, the transmitted absolute attitude of the first handling part and the transmitted absolute attitude of the second handling part are acquired, the absolute attitude of the first handling part and the absolute attitude of the second handling part are consolidated, and the attitude of the treating part is controlled in accordance with the consolidation result, thereby ensuring that the slave manipulator is remotely controlled easily and highly accurately.

In the master manipulator, the method for controlling the master manipulator, and the second storage medium in which the program is stored, according to the present invention, the attitude of the handling part is detected, the detected attitude of the handling part is transmitted to the slave manipulator, and the slave manipulator is controlled in accordance with the consolidation of the attitude of the handling part and the attitude of the handling part of another master manipulator supplied from said another master manipulator so that the treating part of the slave manipulator correctly processes the object, thereby ensuring that the slave manipulator is remotely controlled easily and highly accurately.

In the slave manipulator, the method for controlling the slave manipulator, and the third storage medium in which the program is stored, according to the present invention, the attitude of the first handling part of the first master manipulator transmitted from the first master manipulator and the attitude of the second handling part of the second master manipulator transmitted from the second master manipulator are acquired, the attitude of the first handling part and the attitude of the second handling part are consolidated, and the attitude of the treating part is controlled in accordance with the consolidation result, thereby ensuring that the slave manipulator is remotely controlled easily and highly accurately.

What is claimed is:

1. A manipulator system comprising a first master manipulator including a first handling part handled by a first operator, a second master manipulator including a second handling part handled by a second operator, and a slave manipulator including a treating part for treating an object, the first master manipulator comprising:
   first detection means for detecting an absolute attitude, in a space within which the first handling part is allowed to move, of the first handling part; and
   first transmission means for transmitting the absolute attitude of the first handling part;

the second master manipulator comprising:
   second detection means for detecting an absolute attitude, in a space within which the second handling part is allowed to move, of the second handling part; and
   second transmission means for transmitting the absolute attitude of the second handling part;

the slave manipulator comprising:
   first acquisition means for acquiring the absolute attitude of the first handling part transmitted from the first transmission means of the first master manipulator, and the absolute attitude of the second handling part transmitted from the second transmission means of the first master manipulator;
   first consolidation means for consolidating the absolute attitude of the first handling part and the absolute attitude of the second handling part; and
   first control means for controlling the attitude of the treating part in accordance with the result of the consolidation performed by the first consolidation means.

2. A manipulator system according to claim 1, wherein the absolute attitude of the first handling part is the position and the state, of the first handling part, in a space within which the first handling part is allowed to move, and
   the absolute attitude of the second handling part is the position and the state, of the second handling part, in a space within which the second handling part is allowed to move.

3. A manipulator system according to claim 1, wherein the first consolidation means of the slave manipulator calculates the weighted sum of the absolute attitude of the first handling part and the absolute attitude of the second handling part, using predetermined weighting factors for respective terms.

4. A manipulator system according to claim 1, wherein
   the save manipulator further comprises:
      third detection means for detecting a first force or a first torque applied to the treating part from the object being treated; and
      third transmission means for transmitting the first force or the first torque,
   the first master manipulator further comprises:
      second acquisition means for acquiring the first force or the first torque transmitted from the third transmission means of the slave manipulator;
      first determination means for determining a second force or a second torque to be perceived by the first operator, in accordance with the first force or the first torque acquired by the second acquisition means; and second control means for controlling the first handling part so that the first operator perceives the second force or the second torque, and the second master manipulator further comprises:

third acquisition means for acquiring the first force or the first torque transmitted from the third transmission means of the slave manipulator;

second determination means for determining a third force or a third torque to be perceived by the second operator, in accordance with the first force or the first torque acquired by the third acquisition means; and third control means for controlling the second handling part so that the second operator perceives the third force or the third torque.

5. A manipulator system according to claim 1, wherein the slave manipulator further comprises third transmission means for transmitting the result of the consolidation performed by the first consolidation means, the first master manipulator further comprises:

second acquisition means for acquiring the result of the consolidation transmitted from the third transmission means of the slave manipulator;

first calculation means for calculating the difference between the absolute attitude of the first handling part and the result of the consolidation acquired by the second acquisition means;

first determination means for determining a force or a torque to be perceived by the first operator, in accordance with the result of the calculation performed by the first calculation means; and second control means for controlling the first handling part so that the first operator perceives the force or the torque determined by the first determination means, the second master manipulator further comprises:

third acquisition means for acquiring the result of the consolidation transmitted from the third transmission means of the slave manipulator;

second calculation means for calculating the difference between the absolute attitude of the second handling part and the result of the consolidation acquired by the third acquisition means;

second determination means for determining a force or a torque to be perceived by the second operator, in accordance with the result of the calculation performed by the second calculation means; and third control means for controlling the second handling part so that the second operator perceives the force or the torque determined by the second determination means.

6. A manipulator system according to claim 1, wherein the slave manipulator further comprises:

third detection means for detecting a first force or a first torque applied to the treating part from the object being treated; and third transmission means for transmitting the first force or the first torque and the result of the consolidation performed by the first consolidation means, the first master manipulator further comprises:

second acquisition means for acquiring the first force or the first torque and the result of the consolidation transmitted from the third transmission means of the slave manipulator;

first calculation means for calculating the difference between the absolute attitude of the first handling part and the result of the consolidation acquired by the second acquisition means;

first determination means for determining a second force or a second torque to be perceived by the first operator, in accordance with the first force or the first torque acquired by the second acquisition means and in accordance with the difference calculated by the first calculation means; and second control means for controlling the first handling part so that the first operator perceives the second force or the second torque, the second master manipulator further comprises:

third acquisition means for acquiring the first force or the first torque and the result of the consolidation transmitted from the third transmission means of the slave manipulator;

second calculation means for calculating the difference between the absolute attitude of the second handling part and the result of the consolidation acquired by the third acquisition means;

second determination means for determining a third force or a third torque to be perceived by the second operator, in accordance with the first force or the first torque acquired by the third acquisition means and in accordance with the difference calculated by the second calculation means; and third control means for controlling the second handling part so that the second operator perceives the third force or the third torque.

7. A manipulator system according to claim 1, wherein the first master manipulator further comprises first display control means for controlling a cue so that the first operator can operate the first handling part in synchronization with the operation of the second operator on the second handling part in accordance with the cue, and the second master manipulator further comprises second display control means for controlling the cue so that the second operator can operate the second handling part in synchronization with the operation of the first operator on the first handling part in accordance with the cue.

8. A manipulator system according to claim 1, wherein the first master manipulator further comprises first output control means for controlling a sound/voice cue so that the first operator can operate the first handling part in synchronization with the operation of the second operator on the second handling part in accordance with the sound/voice cue, and the second master manipulator further comprises second output control means for controlling the sound/voice cue so that the second operator can operate the second handling part in synchronization with the operation of the first operator on the first handling part in accordance with the sound/voice cue.

9. A manipulator system according to claim 1, further comprising a third master manipulator including a third handling part handled by a third operator, wherein the third master manipulator further includes:

third detection means for detecting a relative attitude of the third handling part with respect to a predetermined reference attitude; and third transmission means for transmitting the relative attitude of the third handling part detected by the third detection means, the first acquisition means of the slave manipulator further acquires the relative attitude of the third handling part transmitted from the third transmission means of the third master manipulator, and the first consolidation means consolidates the absolute attitude of the first handling part, the absolute attitude of the second handling part, and the relative attitude of the third handling part.

10. A manipulator system according to claim 9, wherein the first consolidation means of the slave manipulator calculates the weighted sum of the absolute attitude of the first handling part, the absolute attitude of the second handling part, and the relative attitude of the third handling part, using predetermined weighting factors for respective terms.

11. A manipulator system according to claim 9, wherein the slave manipulator further comprises:
fourth detection means for detecting a first force or a first torque applied to the treating part from the object being treated; and
fourth transmission means for transmitting the first force or the first torque,
the first manipulator further comprises:
second acquisition means for acquiring the first force or the first torque transmitted from the fourth transmission means of the slave manipulator;
third acquisition means for acquiring the absolute attitude of the second handling part transmitted of the second transmission means of the second master manipulator;
second consolidation means for consolidating the absolute attitude of the first handling part and the absolute attitude of the second handling part;
first calculation means for calculating the difference between the absolute attitude of the first handling part and the result of the consolidation performed by the second consolidation means;
first determination means for determining a second force or a second torque to be perceived by the first operator, in accordance with the first force or the first torque acquired by the second acquisition means and in accordance with the difference calculated by the first calculation means; and
second control means for controlling the first handling part so that the first operator perceives the second force or the second torque,
the second master manipulator further comprises:
fourth acquisition means for acquiring the first force or the first torque transmitted from the fourth transmission means of the slave manipulator;
fifth acquisition means for acquiring the absolute attitude of the first handling part transmitted of the first transmission means of the first master manipulator;
third consolidation means for consolidating the absolute attitude of the second handling part and the absolute attitude of the first handling part;
second calculation means for calculating the difference between the absolute attitude of the second handling part and the result of the consolidation performed by the third consolidation means;
second determination means for determining a third force or a third torque to be perceived by the second operator, in accordance with the first force or the first torque acquired by the fourth acquisition means and in accordance with the difference calculated by the second calculation means; and
third control means for controlling the second handling part so that the second operator perceives the third force or the third torque, and
the third master manipulator further comprises:
sixth acquisition means for acquiring the first force or the first torque transmitted from the fourth transmission means of the slave manipulator;
third determination means for determining a fourth force or a fourth torque to be perceived by the third operator, in accordance with the first force or the first torque acquired by the sixth acquisition means and in accordance with the relative attitude of the third handling part; and
fourth control means for controlling the third handling part so that the third operator perceives the fourth force or the fourth torque.

12. A manipulator system according to claim 11, wherein
the first master manipulator further comprises seventh acquisition means for acquiring the relative attitude of the third handling part transmitted from the third transmission means of the third master manipulator,
the first determination means of the first master manipulator determines the second force or the second torque such that if a value corresponding to the relative attitude of the third handling part is smaller than a predetermined threshold value, the second force or the second torque is determined in accordance with the first force or the first torque and the result of the consolidation performed by the second consolidation means, however if the value corresponding to the relative attitude of the third handling part is equal to or greater than the predetermined threshold value, the second force or the second torque is determined in accordance with only the result of the consolidation performed by the second consolidation means,
the second master manipulator further comprises eighth acquisition means for acquiring the relative attitude of the third handling part transmitted from the third transmission means of the third master manipulator,
the second determination means of the second master manipulator determines the third force or the third torque such that if the value corresponding to the relative attitude of the third handling part is smaller than the predetermined threshold value, the third force or the third torque is determined in accordance with the first force or the first torque and the result of the consolidation performed by the third consolidation means, however if the value corresponding to the relative attitude of the third handling part is equal to or greater than the predetermined threshold value, the third force or the third torque is determined in accordance with only the result of the consolidation performed by the third consolidation means, and
the third determination means of the third master manipulator determines the fourth force or the fourth torque such that if the value corresponding to the relative attitude of the third handling part is smaller than the predetermined threshold value, the fourth force or the fourth torque is determined in accordance with only the relative attitude of the third handling part, however if the value corresponding to the relative attitude of the third handling part is equal to or greater than the predetermined threshold value, the fourth force or the fourth torque is determined in accordance with the relative attitude of the third handling part and the first force or the first torque.

13. A manipulator control method in a manipulator system including a first master manipulator including a first handling part handled by a first operator, a second master manipulator including a second handling part handled by a second operator, and a slave manipulator including a treating part for treating an object, the method comprising:
a first detection step for detecting an absolute attitude, in a space within which the first handling part is allowed to move, of the first handling part of the first master manipulator;

a first transmission step for transmitting the absolute attitude of the first handling part;

a second detection step for detecting an absolute attitude, in a space within which the second handling part is allowed to move, of the second handling part of the second master manipulator;

a second transmission step for transmitting the absolute attitude of the second handling part;

a first acquisition step for acquiring the absolute attitude of the first handling part transmitted in the first transmission step and the absolute attitude of the second handling part transmitted in the second transmission step;

a first consolidation step for consolidating the absolute attitude of the first handling part and the absolute attitude of the second handling part; and a first control step for controlling the attitude of the treating part in accordance with the result of the consolidation performed in the first consolidation step.

14. A manipulator control method according to claim 13, wherein the absolute attitude of the first handling part is the position and the state, of the first handling part, in a space within which the first handling part is allowed to move, and the absolute attitude of the second handling part is the position and the state, of the second handling part, in a space within which the second handling part is allowed to move.

15. A manipulator control method according to claim 13, wherein the first consolidation step calculates the weighted sum of the absolute attitude of the first handling part and the absolute attitude of the second handling part, using predetermined weighting factors for respective terms.

16. A manipulator control method according to claim 13, further comprising:

a third detection step for detecting a first force or a first torque applied to the treating part of the slave manipulator from the object being treated;

a third transmission step for transmitting the first force or the first torque, a second acquisition step for acquiring the first force or the first torque transmitted in the third transmission step;

a first determination step for determining a second force or a second torque to be perceived by the first operator, in accordance with the first force or the first torque acquired in the second acquisition step;

a second control step for controlling the first handling part so that the first operator perceives the second force or the second torque, a third acquisition step for acquiring the first force or the first torque transmitted in the third transmission step;

a second determination step for determining a third force or a third torque to be perceived by the second operator, in accordance with the first force or the first torque acquired in the third acquisition step; and a third control step for controlling the second handling part so that the second operator perceives the third force or the third torque.

17. A manipulator control method according to claim 13, further comprising:

a third transmission step for transmitting the result of the consolidation performed in the first consolidation step;

a second acquisition step for acquiring the result of the consolidation transmitted in the third transmission step;

a first calculation step for calculating the difference between the absolute attitude of the first handling part and the result of the consolidation acquired in the second acquisition step;

a first determination step for determining a force or a torque to be perceived by the first operator, in accordance with the result of the calculation performed in the first calculation step;

a second control step for controlling the first handling part so that the first operator perceives the force or the torque determined in the first determination step;

a third acquisition step for acquiring the result of the consolidation transmitted in the third transmission step;

a second calculation step for calculating the difference between the absolute attitude of the second handling part and the result of the consolidation acquired in the third acquisition step;

a second determination step for determining a force or a torque to be perceived by the second operator, in accordance with the result of the calculation performed in the second calculation step; and a third control step for controlling the second handling part so that the second operator perceives the force or the torque determined in the second determination step.

18. A manipulator control method according to claim 13, further comprising:

a third detection step for detecting a first force or a first torque applied to the treating part of the slave manipulator from the object being treated;

a third transmission step for transmitting the first force or the first torque and the result of the consolidation performed in the first consolidation step;

a second acquisition step for acquiring the first force or the first torque and the result of the consolidation transmitted in the third transmission step;

a first calculation step for calculating the difference between the absolute attitude of the first handling part and the result of the consolidation acquired in the second acquisition step;

a first determination step for determining a second force or a second torque to be perceived by the first operator, in accordance with the first force or the first torque acquired in the second acquisition step and in accordance with the difference calculated in the first calculation step;

a second control step for controlling the first handling part so that the first operator perceives the second force or the second torque;

a third acquisition step for acquiring the first force or the first torque and the result of the consolidation transmitted in the third transmission step;

a second calculation step for calculating the difference between the absolute attitude of the second handling part and the result of the consolidation acquired in the third acquisition step;

a second determination step for determining a third force or a third torque to be perceived by the second operator, in accordance with the first force or the first torque acquired in the third acquisition step and in accordance with the difference calculated in the second calculation step; and a third control step for controlling the second handling part so that the second operator perceives the third force or the third torque.

19. A manipulator control method according to claim 13, further comprising:
- a first display control step for controlling a cue so that the first operator can operate the first handling part in synchronization with the operation of the second operator on the second handling part in accordance with the cue, and
- a second display control step for controlling the cue so that the second operator can operate the second handling part in synchronization with the operation of the first operator on the first handling part in accordance with the cue.

20. A manipulator control method according to claim 13, further comprising:
- a first output control step for controlling a sound/voice cue so that the first operator can operate the first handling part in synchronization with the operation of the second operator on the second handling part in accordance with the sound/voice cue, and
- a second display control step for controlling the cue so that the second operator can operate the second handling part in synchronization with the operation of the first operator on the first handling part in accordance with the cue.

21. A manipulator control method according to claim 13, wherein the manipulator system further includes a third master manipulator including a third handling part handled by a third operator, and the method further comprises:
- a third detection step for detecting a relative attitude of the third handling part of the third master manipulator with respect to a predetermined reference attitude; and
- a third transmission step for transmitting the relative attitude of the third handling part detected in the third detection step,
- and wherein the first acquisition step further acquires the relative attitude of the third handling part of the third master manipulator transmitted in the third transmission step, and
- the first consolidation step consolidates the absolute attitude of the first handling part, the absolute attitude of the second handling part, and the relative attitude of the third handling part.

22. A manipulator control method according to claim 21, wherein the first consolidation step calculates the weighted sum of the absolute attitude of the first handling part, the absolute attitude of the second handling part, and the relative attitude of the third handling part, using predetermined weighting factors for respective terms.

23. A manipulator control method according to claim 21, further comprising:
- a fourth detection step for detecting a first force or a first torque applied to the treating part of the slave manipulator from the object being treated;
- a fourth transmission step for transmitting the first force or the first torque,
- a second acquisition step for acquiring the first force or the first torque transmitted in the fourth transmission step;
- a third acquisition step for acquiring the absolute attitude of the second handling part transmitted in the second transmission step;
- a second consolidation step for consolidating the absolute attitude of the first handling part and the absolute attitude of the second handling part;
- a first calculation step for calculating the difference between the absolute attitude of the first handling part and the result of the consolidation performed in the second consolidation step;
- a first determination step for determining a second force or a second torque to be perceived by the first operator, in accordance with the first force or the first torque acquired in the second acquisition step and in accordance with the difference calculated in the first calculation step;
- a second control step for controlling the first handling part so that the first operator perceives the second force or the second torque;
- a fourth acquisition step for acquiring the first force or the first torque transmitted in the fourth transmission step;
- a fifth acquisition step for acquiring the absolute attitude of the first handling part transmitted in the first transmission step;
- a third consolidation step for consolidating the absolute attitude of the first handling part and the absolute attitude of the second handling part;
- a second calculation step for calculating the difference between the absolute attitude of the second handling part and the result of the consolidation performed in the third consolidation step;
- a second determination step for determining a third force or a third torque to be perceived by the second operator, in accordance with the first force or the first torque acquired in the fourth acquisition step and in accordance with the difference calculated in the second calculation step;
- a third control step for controlling the second handling part so that the second operator perceives the third force or the third torque;
- a sixth acquisition step for acquiring the first force or the first torque transmitted in the fourth transmission step;
- a third determination step for determining a fourth force or a fourth torque to be perceived by the third operator, in accordance with the first force or the first torque acquired in the sixth acquisition step and in accordance with the relative attitude of the third handling part; and
- a fourth control step for controlling the third handling part so that the third operator perceives the fourth force or the fourth torque.

24. A manipulator control method according to claim 23, the method further comprising: a seventh acquisition step for acquiring the relative attitude of the third handling part transmitted in the third transmission step,
- wherein the first determination step determines the second force or the second torque such that if a value corresponding to the relative attitude of the third handling part is smaller than a predetermined threshold value, the second force or the second torque is determined in accordance with the first force or the first torque and the result of the consolidation performed in the second consolidation step, however if the value corresponding to the relative attitude of the third handling part is equal to or greater than the predetermined threshold value, the second force or the second torque is determined in accordance with only the result of the consolidation performed in the second consolidation step,
- the method further comprising an eighth acquisition step for acquiring the relative attitude of the third handling part transmitted in the third transmission step,
- wherein the second determination step determines the third force or the third torque such that if a value corresponding to the relative attitude of the third handling part is smaller than a predetermined threshold value, the third force or the third torque is determined in accordance with the first force or the first torque and the result of the consolidation performed in the third consolidation step, however if the value corresponding to the relative attitude of the third handling part is equal to or greater than the predetermined threshold value, the third force or the third torque is determined in accordance with only the result of the consolidation performed in the third consolidation step, and wherein the third determination step determines the fourth force or the fourth torque such that if a value corresponding to the relative attitude of the third handling part is smaller than a predetermined threshold value, the fourth force or the fourth torque is determined in accordance with the value corresponding to the relative attitude of the third handling part, however if the value corresponding to the relative attitude of the third handling part is equal to or greater than the predetermined threshold value, the fourth force or the fourth torque is determined in accordance with the value corresponding to the relative attitude of the third handling part and the first force or the first torque.

25. A storage medium in which is stored a computer-readable program for controlling a manipulator system including a first master manipulator including a first handling part handled by a first operator, a second master manipulator including a second handling part handled by a second operator, and a slave manipulator including a treating part for treating an object, the program comprising:

a first detection step for detecting an absolute attitude, in a space within which the first handling part is allowed to move, of the first handling part of the first master manipulator;

a first transmission step for transmitting the absolute attitude of the first handling part;

a second detection step for detecting an absolute attitude, in a space within which the second handling part is allowed to move, of the second handling part of the second master manipulator;

a second transmission step for transmitting the absolute attitude of the second handling part;

a first acquisition step for acquiring the absolute attitude of the first handling part transmitted in the first transmission step and the absolute attitude of the second handling part transmitted in the second transmission step;

a first consolidation step for consolidating the absolute attitude of the first handling part and the absolute attitude of the second handling part; and a first control step for controlling the attitude of the treating part in accordance with the result of the consolidation performed in the first consolidation step.

26. A master manipulator having a handling part handled by an operator, the master manipulator comprising:

detection means for detecting the attitude of the handling part; and transmission means for transmitting the attitude of the handling part to a slave manipulator thereby allowing the slave manipulator to control a treating part of the slave manipulator so as to process an object in accordance with a result of consolidation of the attitude of the handling part and the attitude of a handling part of another master manipulator supplied from said another master manipulator.

27. A method for controlling a master manipulator having a handling part handled by an operator, the method comprising:

a detection step for detecting the attitude of the handling part; and a transmission step for transmitting the attitude of the handling part to a slave manipulator thereby allowing the slave manipulator to control a treating part of the slave manipulator so as to process an object in accordance with a result of consolidation of the attitude of the handling part and the attitude of a handling part of another master manipulator supplied from said another master manipulator.

28. A storage medium in which is stored a computer-readable program for controlling a master manipulator having a handling part handled by an operator, the program comprising:

a detection step for detecting the attitude of the handling part; and a transmission step for transmitting the attitude of the handling part to a slave manipulator thereby allowing the slave manipulator to control a treating part of the slave manipulator so as to process an object in accordance with a result of consolidation of the attitude of the handling part and the attitude of a handling part of another master manipulator supplied from said another master manipulator.

29. A slave manipulator having a treating part for treating an object, the salve manipulator comprising:

acquisition means for acquiring the attitude of a first handling part of a first master manipulator transmitted from the first master manipulator and the attitude of a second handling part of a second master manipulator transmitted from the second master manipulator;

consolidation means for consolidating the attitude of the first handling part and the attitude of the second handling part; and control means for controlling the attitude of the treating part in accordance with the result of the consolidation performed by the consolidation means.

30. A method for controlling a slave manipulator having a treating part for treating an object, the method comprising:

an acquisition step for acquiring the attitude of a first handling part of a first master manipulator transmitted from the first master manipulator and the attitude of a second handling part of a second master manipulator transmitted from the second master manipulator;

a consolidation step for consolidating the attitude of the first handling part and the attitude of the second handling part; and a control step for controlling the attitude of the treating part in accordance with the result of the consolidation performed in the consolidation step.

31. A storage medium in which is stored a computer-readable program for controlling a slave manipulator having a treating part for treating an object, the program comprising:

an acquisition step for acquiring the attitude of a first handling part of a first master manipulator transmitted from the first master manipulator and the attitude of a second handling part of a second master manipulator transmitted from the second master manipulator;

a consolidation step for consolidating the attitude of the first handling part and the attitude of the second handling part; and a control step for controlling the attitude of the treating part in accordance with the result of the consolidation performed in the consolidation step.

\* \* \* \* \*